United States Patent
Walton et al.

(10) Patent No.: US 12,194,026 B2
(45) Date of Patent: Jan. 14, 2025

(54) DRUG FOR TREATING TINNITUS

(71) Applicant: UNIVERSITY OF SOUTH FLORIDA, Tampa, FL (US)

(72) Inventors: Joseph P. Walton, Tampa, FL (US); Luisa Lynn Scott, Austin, TX (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 759 days.

(21) Appl. No.: 17/288,718

(22) PCT Filed: Aug. 26, 2019

(86) PCT No.: PCT/US2019/048074
§ 371 (c)(1),
(2) Date: Apr. 26, 2021

(87) PCT Pub. No.: WO2020/086149
PCT Pub. Date: Apr. 30, 2020

(65) Prior Publication Data
US 2021/0393596 A1 Dec. 23, 2021

Related U.S. Application Data

(60) Provisional application No. 62/751,214, filed on Oct. 26, 2018.

(51) Int. Cl.
*A61K 31/4245* (2006.01)
*A61P 25/00* (2006.01)
*A61P 27/16* (2006.01)

(52) U.S. Cl.
CPC .......... *A61K 31/4245* (2013.01); *A61P 25/00* (2018.01); *A61P 27/16* (2018.01)

(58) Field of Classification Search
CPC ....... A61K 31/4245; A61P 25/00; A61P 27/16
See application file for complete search history.

(56) References Cited

U.S. PATENT DOCUMENTS

| 2002/0045651 A1 | 4/2002 | Brenner et al. |
| 2003/0069292 A1 | 4/2003 | Hogenkamp et al. |

(Continued)

FOREIGN PATENT DOCUMENTS

| WO | WO1998004135 A1 * | 2/1998 | ........... C07D 248/12 |
| WO | 1999038510 | 8/1999 | |
| WO | 2005049042 A1 | 6/2005 | |

OTHER PUBLICATIONS

Lobarinas, Edward, et al. "Effects of the Potassium Ion Channel Modulators BMS-204352 Maxipost and Its R-Enantiomer on Salicylate-Induced Tinnitus in Rats." Physiology & Behavior, vol. 104, No. 5, Oct. 2011, pp. 873-879. Science Direct, https://doi.org/10.1016/j.physbeh.2011.05.022. (Year: 2011).*

(Continued)

*Primary Examiner* — Clinton A Brooks
*Assistant Examiner* — Kyle Nottingham
(74) *Attorney, Agent, or Firm* — Meunier Carlin & Curfman LLC

(57) ABSTRACT

Compounds, pharmaceutical compositions, and methods for treating tinnitus in a subject in need thereof. The methods include administering a therapeutically effective amount of a compound having a structure represented by Formula I as described herein. The compounds and compositions are administered transdermally or orally, preferably via a sustained release mechanism. The compounds and compositions reduce at least one behavioral correlate of tinnitus and/or at least one neurophysiological correlate of tinnitus. The compounds and compositions reduce hyperactivity in the auditory system.

13 Claims, 6 Drawing Sheets

(56) References Cited

U.S. PATENT DOCUMENTS

2016/0326150 A1 11/2016 Jakob-Roetne et al.
2018/0127357 A1 5/2018 Wipf et al.

OTHER PUBLICATIONS

Nardi, Antonio, and Søren-Peter Olesen. "BK Channel Modulators: A Comprehensive Overview." Current Medicinal Chemistry, vol. 15, No. 11, 2008, pp. 1126-1146. PubMed, https://doi.org/10.2174/092986708784221412. (Year: 2008).*
Brown, Marc B., et al. "Dermal and Transdermal Drug Delivery Systems: Current and Future Prospects." Drug Delivery, vol. 13, No. 3, Jan. 2006, pp. 175-187. DOI.org (Crossref), https://doi.org/10.1080/10717540500455975. (Year: 2006).*
Hewawasam, Piyasena, et al. "Synthesis of Water-Soluble Prodrugs of BMS-191011: A Maxi-K Channel Opener Targeted for Post-Stroke Neuroprotection." Bioorganic & Medicinal Chemistry Letters, vol. 13, No. 10, May 2003, pp. 1695-1698. Science Direct, https://doi.org/10.1016/S0960-894X(03)00296-8. (Year: 2003).*
International Preliminary Report on Patentability issued for Application No. PCT/US2019/048074, dated May 6, 2021.
Allen, P.D., Burkard, R.F., Ison, J.R., and Walton, J.P. (2003). Impaired gap encoding in aged mouse inferior colliculus at moderate but not high stimulus levels. Hear Res 186, 17-29.
Bentzen, B.H., Olesen, S.P., Ronn, L.C., and Grunnet, M. (2014). BK channel activators and their therapeutic perspectives. Front Physiol 5, 389.
Berge, Stephen M., Lyle D. Bighley, and Donald C. Monkhouse. "Pharmaceutical salts." Journal of pharmaceutical sciences 66.1 (1977): 1-19.
Berger, J.I., Coomber, B., Shackleton, T.M., Palmer, A.R., and Wallace, M.N. (2013). A novel behavioural approach to detecting tinnitus in the guinea pig. Journal of neuroscience methods 213, 188-195.
Brenner, R., and Wilcox, K. (2012a). Potassium Channelopathies of Epilepsy. In Jasper's Basic Mechanisms of the Epilepsies, J. Noebels, M. Avoli, M. Rogawski, and e. al., eds. (Bethesda (MD): National Center for Biotechnology Information (US), 16 pages.
Brenner, R., Chen, Q.H., Vilaythong, A., Toney, G.M., Noebels, J.L., and Aldrich, R.W. (2005). BK channel beta4 subunit reduces dentate gyrus excitability and protects against temporal lobe seizures. Nature neuroscience 8, 1752-1759.
Brown, M.R., and Kaczmarek, L.K. (2011). Potassium channel modulation and auditory processing. Hearing Research 279, 32-42.
Chang, C.P., Dworetzky, S.I., Wang, J., and Goldstein, M.E. (1997). Differential expression of the alpha and beta subunits of the large-conductance calcium-activated potassium channel: implication for channel diversity. Brain Res Mol Brain Res 45, 33-40.
Chen, G.-d., and Jastreboff, P.J. (1995). Salicylate-induced abnormal activity in the inferior colliculus of rats. Hearing Research 82, 158-178.
Chen, G.-D., Stolzberg, D., Lobarinas, E., Sun, W., Ding, D., and Salvi, R. (2013). Salicylate-induced cochlear impairments, cortical hyperactivity and re-tuning, and tinnitus. Hearing Research 295, 100-113.
Contet, C., Goulding, S.P., Kuljis, D.A., and Barth, A.L. (2016). BK Channels in the Central Nervous System. In International Review of Neurobiology (Academic Press), pp. 281-342.
Ding, B., Sakai, Y., Scott, L.L., Zhu, X., Yuan, Y., and Walton, J.P. (2016). Age-related modulation of BK channel phosphorylation and the effects of using specific peptides that modulate BK function. ARO abstract. pp. 15-16.
Eatock, R.A. (2003). Auditory Physiology: Listening with K+ Channels. Current Biology 13, R767-R769.
Eggermont, J.J. (2013). Hearing loss, hyperacusis, or tinnitus: what is modeled in animal research? Hear Res 295, 140-149.
Gordon, J.S., Griest, S.E., Thielman, E.J., Carlson, K.F., Helt, W.J., Lewis, M.S., Blankenship, C., Austin, D., Theodoroff, S.M., and Henry, J.A. (2017). Audiologic characteristics in a sample of recently-separated military Veterans: The Noise Outcomes in Servicemembers Epidemiology Study (Noise Study). Hear Res 349, 21-30.
Gu, J.W., Herrmann, B.S., Levine, R.A., and Melcher, J.R. (2012). Brainstem auditory evoked potentials suggest a role for the ventral cochlear nucleus in tinnitus. Journal of the Association for Research in Otolaryngology : JARO 13, 819-833.
Guitton, M.J., Caston, J., Ruel, J., Johnson, R.M., Pujol, R., and Puel, J.L. (2003). Salicylate induces tinnitus through activation of cochlear NMDA receptors. The Journal of neuroscience : the official journal of the Society for Neuroscience 23, 3944-3952.
Hall, Deborah A., et al. "A balanced randomised placebo controlled blinded phase IIa multi-centre study to investigate the efficacy and safety of AUT00063 versus placebo in subjective tinnitus: The QUIET-1 trial." Hearing research 377 (2019): 153-166.
He, S., Wang, Y.-X., Petralia, R.S., and Brenowitz, S.D. (2014). Cholinergic Modulation of Large-Conductance Calcium-Activated Potassium Channels Regulates Synaptic Strength and Spine Calcium in Cartwheel Cells of the Dorsal Cochlear Nucleus. The Journal of Neuroscience 34, 5261-5272.
Henry, J.A., Roberts, L.E., Caspary, D.M., Theodoroff, S.M., and Salvi, R.J. (2014). Underlying mechanisms of tinnitus: review and clinical implications. J Am Acad Audiol 25, 5-22; quiz 126.
Hewawasam, P., Gribkoff, V.K., Pendri, Y., Dworetzky, S.I., Meanwell, N.A., Martinez, E., Boissard, C.G., Post-Munson, D.J., Trojnacki, J.T., Yeleswaram, K., et al. (2002). The synthesis and characterization of BMS-204352 (MaxiPost) and related 3-fluorooxindoles as openers of maxi-K potassium channels. Bioorg Med Chem Lett 12, 1023-1026.
Hickox, A.E., and Liberman, M.C. (2014). Is noise-induced cochlear neuropathy key to the generation of hyperacusis or tinnitus? J Neurophysiol 111, 552-564.
Hoffman, H.S., and Ison, J.R. (1980). Reflex modification in the domain of startle: I. Some empirical findings and their implications for how the nervous system processes sensory input. Psychol Rev 87, 175-189.
Ison, J.R., and Hoffman, H.S. (1983). Reflex modification in the domain of startle: II. The anomalous history of a robust and ubiquitous phenomenon. Psychol Bull 94, 3-17.
Ison, J.R., O'Connor, K., Bowen, G.P., and Bocirnea, A. (1991). Temporal resolution of gaps in noise by the rat is lost with functional decortication. Behav Neurosci 105, 33-40.
Jastreboff, P.J., and Sasaki, C.T. (1986). Salicylate-induced changes in spontaneous activity of single units in the inferior colliculus of the guinea pig. J Acoust Soc Am 80, 1284-1291.
Jensen, B.S. (2002). BMS-204352: a potassium channel opener developed for the treatment of stroke. CNS Drug Rev 8, 353-360.
Kaltenbach, J.A., Zhang, J., and Finlayson, P. (2005). Tinnitus as a plastic phenomenon and its possible neural underpinnings in the dorsal cochlear nucleus. Hear Res 206, 200-226.
Knaus, H.G., Schwarzer, C., Koch, R.O., Eberhart, A., Kaczorowski, G.J., Glossmann, H., Wunder, F., Pongs, O., Garcia, M.L., and Sperk, G. (1996). Distribution of high-conductance Ca(2+)-activated K+ channels in rat brain: targeting to axons and nerve terminals. The Journal of neuroscience : the official journal of the Society for Neuroscience 16, 955-963.
Knipper, M., Van Dijk, P., Nunes, I., Ruttiger, L., and Zimmermann, U. (2013). Advances in the neurobiology of hearing disorders: recent developments regarding the basis of tinnitus and hyperacusis. Progress in neurobiology 111, 17-33.
Koch, M. (1999). The neurobiology of startle. Progress in neurobiology 59, 107-128.
Korsgaard, M.P., Hartz, B.P., Brown, W.D., Ahring, P.K., Strobaek, D., and Mirza, N.R. (2005). Anxiolytic effects of Maxipost (BMS-204352) and retigabine via activation of neuronal Kv7 channels. J Pharmacol Exp Ther 314, 282-292.
Kyle, B.D., and Braun, A.P. (2014). The regulation of BK channel activity by pre- and post-translational modifications. Frontiers in Physiology 5, 316.
Lang, E.J., Sugihara, I., and Llinás, R. (1997). Differential Roles of Apamin- and Charybdotoxin-Sensitive K$^{+}$ Conductances in the Generation of Inferior Olive Rhythmicity <em> In Vivo</em>. The Journal of Neuroscience 17, 2825.

(56) References Cited

OTHER PUBLICATIONS

Langguth, B., Elgoyhen, A.B., and Schlee, W. (2016). Potassium channels as promising new targets for pharmacologic treatment of tinnitus: Can Internet-based 'crowd sensing' initiated by patients speed up the transition from bench to bedside? Expert Opin Ther Targets 20, 251-254.
Leitner, D.S., and Cohen, M.E. (1985). Role of the inferior colliculus in the inhibition of acoustic startle in the rat. Physiology & behavior 34, 65-70.
Li, S., Choi, V., and Tzounopoulos, T. (2013). Pathogenic plasticity of Kv7.2/3 channel activity is essential for the induction of tinnitus. Proc Natl Acad Sci U S A 110, 9980-9985.
Li, S., Kalappa, B.I., and Tzounopoulos, T. (2015). Noise-induced plasticity of KCNQ2/3 and HCN channels underlies vulnerability and resilience to tinnitus. eLife 4, e07242.
Li, X., Poschmann, S., Chen, Q., Fazeli, W., Oundjian, N.J., Snoeijen-Schouwenaars, F.M., Fricke, O., Kamsteeg, E.J., Willemsen, M., and Wang, Q.K. (2018). De novo BK channel variant causes epilepsy by affecting voltage gating but not Ca(2+) sensitivity. Eur J Hum Genet 26, 220-229.
Lobarinas, E., Dalby-Brown, W., Stolzberg, D., Mirza, N.R., Allman, B.L., and Salvi, R. (2011). Effects of the potassium ion channel modulators BMS-204352 Maxipost and its R-enantiomer on salicylate-induced tinnitus in rats. Physiology & behavior 104, 873-879.
Lobarinas, E., Hayes, S.H., and Allman, B.L. (2013). The gap-startle paradigm for tinnitus screening in animal models: limitations and optimization. Hear Res 295, 150-160.
Longenecker, R.J., and Galazyuk, A.V. (2011). Development of tinnitus in CBA/CaJ mice following sound exposure. Journal of the Association for Research in Otolaryngology : JARO 12, 647-658.
Longenecker, R.J., and Galazyuk, A.V. (2012). Methodological optimization of tinnitus assessment using prepulse inhibition of the acoustic startle reflex. Brain Res 1485, 54-62.
Longenecker, R.J., Chonko, K.T., Maricich, S.M., and Galazyuk, A.V. (2014). Age effects on tinnitus and hearing loss in CBA/CaJ mice following sound exposure. Springerplus 3, 542.
Lorenz, S., Heils, A., Kasper, J.M., and Sander, T. (2007). Allelic association of a truncation mutation of the KCNMB3 gene with idiopathic generalized epilepsy. Am J Med Genet B Neuropsychiatr Genet 144B, 10-13.
Lowe, A.S., and Walton, J.P. (2015). Alterations in peripheral and central components of the auditory brainstem response: a neural assay of tinnitus. PloS one 10, e0117228.
Nakamura, Y., and Takahashi, T. (2007). Developmental changes in potassium currents at the rat calyx of Held presynaptic terminal. The Journal of Physiology 581, 1101-1112.
N'Gouemo, P. (2011). Targeting BK (big potassium) channels in epilepsy. Expert Opinion on Therapeutic Targets 15, 1283-1295.
N'Gouemo, P. (2014). BKCa channel dysfunction in neurological diseases. Front Physiol 5, 373.
Oak, M.-H., and Yi, E. (2014). Voltage-gated K+ channels contributing to temporal precision at the inner hair cell-auditory afferent nerve fiber synapses in the mammalian cochlea. Archives of Pharmacal Research 37, 821-833.
Ochi, K., and Eggermont, J.J. (1996). Effects of salicylate on neural activity in cat primary auditory cortex. Hear Res 95, 63-76.
Oliver, D., Taberner, A.M., Thurm, H., Sausbier, M., Arntz, C., Ruth, P., Fakler, B., and Liberman, M.C. (2006). The role of BKCa channels in electrical signal encoding in the mammalian auditory periphery. The Journal of neuroscience : the official journal of the Society for Neuroscience 26, 6181-6189.
Puel, J.L., and Guitton, M.J. (2007). Salicylate-induced tinnitus: molecular mechanisms and modulation by anxiety. Prog Brain Res 166, 141-146.
Pyott, S.J., Meredith, A.L., Fodor, A.A., Vázquez, A.E., Yamoah, E.N., and Aldrich, R.W. (2007). Cochlear Function in Mice Lacking the BK Channel α, β1, or β4 Subunits. Journal of Biological Chemistry 282, 3312-3324.
Radziwon, K., Holfoth, D., Lindner, J., Kaier-Green, Z., Bowler, R., Urban, M., and Salvi, R. (2017). Salicylate-induced hyperacusis in rats: Dose- and frequency-dependent effects. Hear Res 350, 133-138.
Romine, J.L., Martin, S.W., Meanwell, N.A., Gribkoff, V.K., Boissard, C.G., Dworetzky, S.I., Natale, J., Moon, S., Ortiz, A., Yeleswaram, S., et al. (2007). 3-[(5-Chloro-2-hydroxyphenyl)methyl]-5-[4-(trifluoromethyl)phenyl ]-1,3,4-oxadiazol-2(3H)-one, BMS-191011: opener of large-conductance Ca(2+)-activated potassium (maxi-K) channels, identification, solubility, and Sar. J Med Chem 50, 528-542.
Sand, P.G., Luettich, A., Kleinjung, T., Hajak, G., and Langguth, B. (2010). An Examination of KCNE1 Mutations and Common Variants in Chronic Tinnitus. Genes 1, 23-37.
Sand, Philipp G., Berthold Langguth, and Tobias Kleinjung. "Deep resequencing of the voltage-gated potassium channel subunit KCNE3 gene in chronic tinnitus." Behavioral and Brain Functions 7.1 (2011): 1-5.
Satas, "The Handbook of Pressure-sensitive Adhesive Technology," 2nd ed., pp. 396-456 (1989).
Sausbier, U., Sausbier, M., Sailer, C.A., Arntz, C., Knaus, H.G., Neuhuber, W., and Ruth, P. (2006). Ca2+ -activated K+ channels of the BK-type in the mouse brain. Histochemistry and cell biology 125, 725-741.
Scott, L.L., Brecht, E.J., Philpo, A., Iyer, S., Wu, N.S., Mihic, S.J., Aldrich, R.W., Pierce, J., and Walton, J.P. (2017). A novel BK channel-targeted peptide suppresses sound evoked activity in the mouse inferior colliculus. Sci Rep 7, 42433.
Sheehan, J., Benedetti, B., and Barth, A. (2009). Anticonvulsant effects of the BK-channel antagonist paxilline. Epilepsia 50, 711-720.
Shipston, M.J., and Tian, L. Posttranscriptional and Post-translational Regulation of BK Channels. In International Review of Neurobiology (Academic Press).
Sivaramakrishnan, S., and Oliver, D.L. (2001). Distinct K Currents Results in Physiologically Distinct Cell Types in the Inferior Colliculus of the Rat. J Neurosci 21, 2861-2877.
Song, P., Yang, Y., Barnes-Davies, M., Bhattacharjee, A., Hamann, M., Forsythe, I.D., Oliver, D.L., and Kaczmarek, L.K. (2005). Acoustic environment determines phosphorylation state of the Kv3.1 potassium channel in auditory neurons. Nature neuroscience 8, 1335-1342.
Stolzberg, D., Salvi, R.J., and Allman, B.L. (2012). Salicylate toxicity model of tinnitus. Frontiers in Systems Neuroscience 6, 28.
Sun, W., Lu, J., Stolzberg, D., Gray, L., Deng, A., Lobarinas, E., and Salvi, R.J. (2009). Salicylate increases the gain of the central auditory system. Neuroscience 159, 325-334.
Syka, J., and Rybalko, N. (2000). Threshold shifts and enhancement of cortical evoked responses after noise exposure in rats. Hear Res 139, 59-68.
Thurm, H., Fakler, B., and Oliver, D. (2005). Ca2+-independent activation of BKCa channels at negative potentials in mammalian inner hair cells. J Physiol 569, 137-151.
Turner, J., Larsen, D., Hughes, L., Moechars, D., and Shore, S. (2012). Time course of tinnitus development following noise exposure in mice. J Neurosci Res 90, 1480-1488.
Turner, J.G. (2007). Behavioral measures of tinnitus in laboratory animals. In Progress in Brain Research, B. Langguth, G. Hajak, T. Kleinjung, A. Cacace, and A.R. Møller, eds. (Elsevier), pp. 147-549.
Wu, C., K, V.G., Lukas, T.J., Gross, G.W., and Moore, E.J. (2014a). Pharmacodynamics of potassium channel openers in cultured neuronal networks. Eur J Pharmacol 732, 68-75.
Yan, J., and Aldrich, R.W. (2012). BK potassium channel modulation by leucine-rich repeat-containing proteins. Proc Natl Acad Sci U S A 109, 7917-7922.
Yang, G., Lobarinas, E., Zhang, L., Turner, J., Stolzberg, D., Salvi, R., and Sun, W. (2007). Salicylate induced tinnitus: Behavioral measures and neural activity in auditory cortex of awake rats. Hearing Research 226, 244-253.
Yoshida, Masaru, et al. "Study of biodegradable copoly (L-lactic acid/glycolic acid) formulations with controlled release of Z-100 for application in radiation therapy." International journal of pharmaceutics 115.1 (1995): 61-67.

(56) References Cited

OTHER PUBLICATIONS

Zhang, X., Yang, P., Cao, Y., Qin, L., and Sato, Y. (2011). Salicylate induced neural changes in the primary auditory cortex of awake cats. Neuroscience 172, 232-245.
International Search Report and Written Opinion in PCT/US2019/048074. Mailed Nov. 18, 2019. 8 pages.
Pubmed Compound Summary for CID 50951330, 3-[2-(2-Hydroxyphenyl)ethyl]-4-[(3-methylphenyl)methyl]-1 H-1,2,4-triazol-5-one, US National Library of Medicine, Mar. 29, 2011, p. 1-15.
Mori et al., BMS-191011, an Opener of Large-Conductance Ca2+-Activated Potassium Channels, Dilates Rat Retinal Arterioles in Vivo, Biol. Pharm. Bull, 34(1), pp. 150-152.
Extended European Search Report issued in EP19876115.7, mailed Jul. 14, 2022.

\* cited by examiner

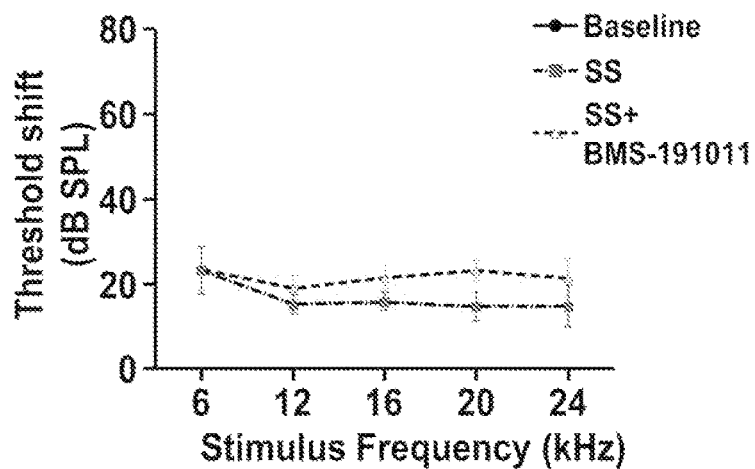
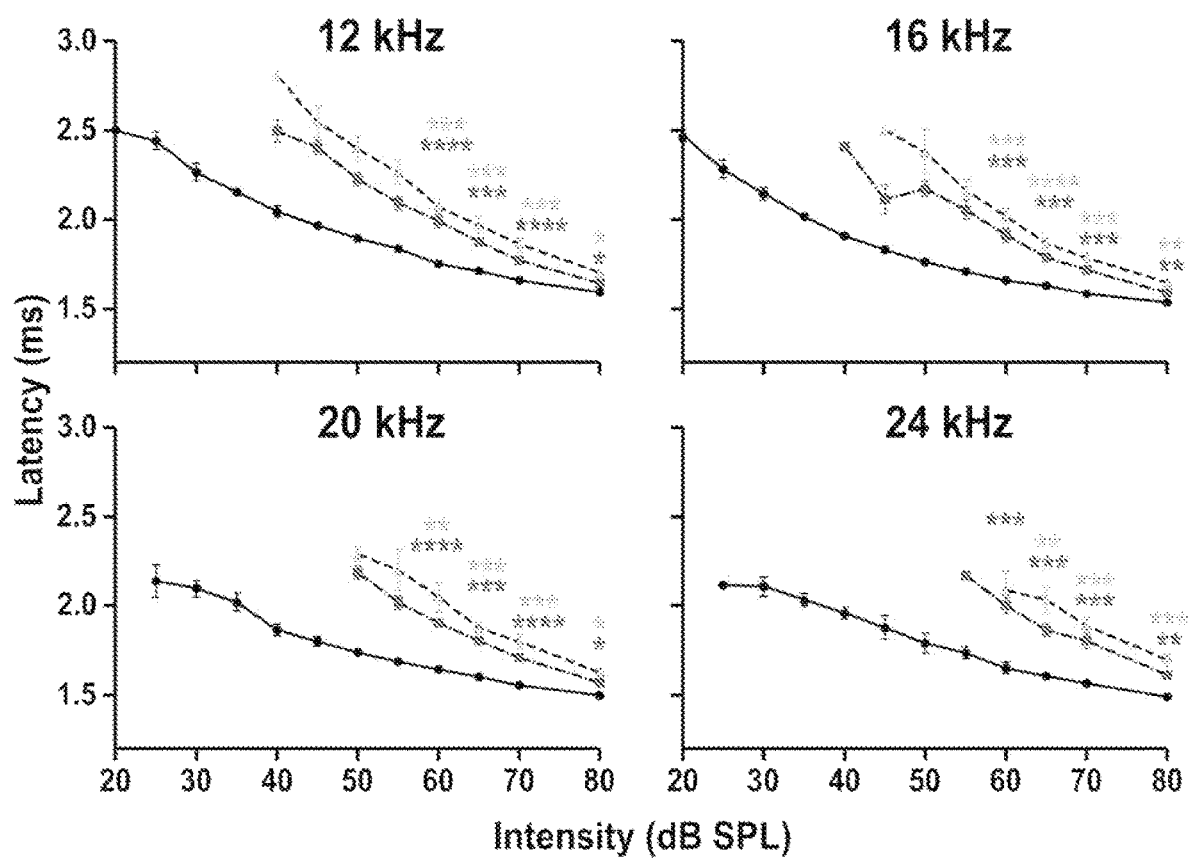
FIGS. 2A-2C c
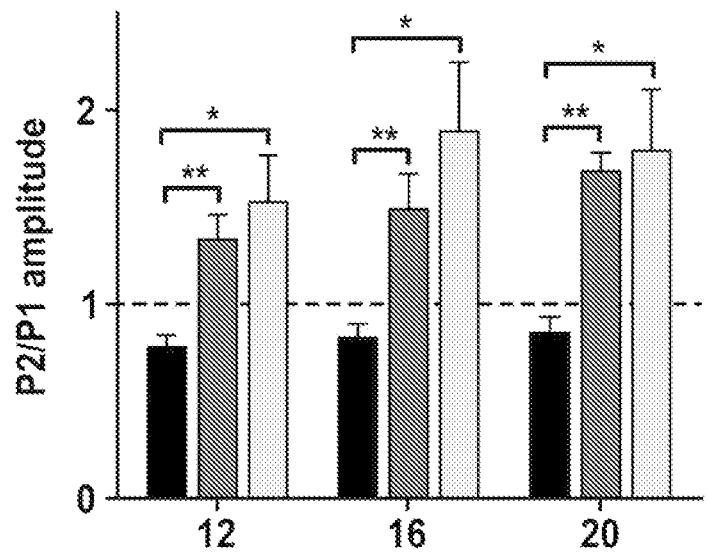
d
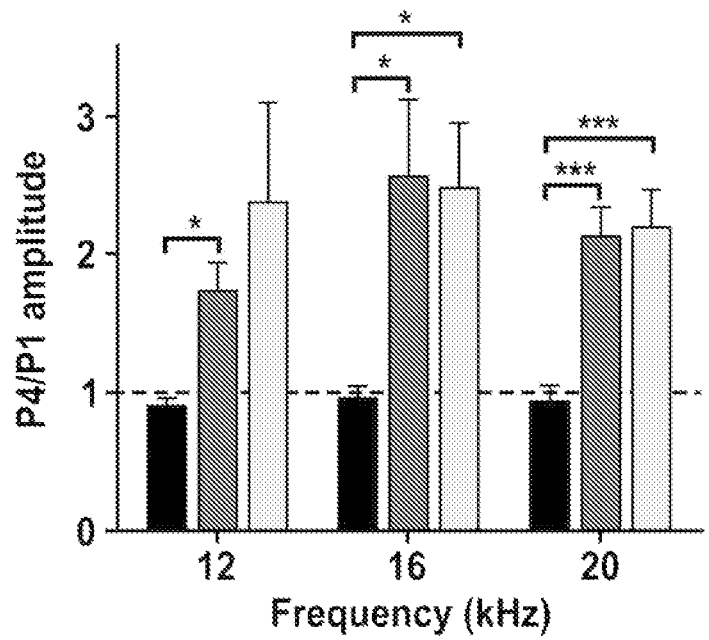
FIGS. 3A-3D CONT.

DRUG FOR TREATING TINNITUS

CROSS REFERENCE TO RELATED APPLICATIONS

This application is a United States National Phase Patent Application of International Patent Application Number PCT/US2019/048074, filed on Aug. 26, 2019, which claims the benefit of priority to U.S. Provisional Application No. 62/751,214 filed Oct. 26, 2018, which is incorporated by reference herein in its entirety.

STATEMENT ACKNOWLEDGING OF GOVERNMENT SUPPORT

This invention was made with government support under grant no. AG009524 awarded by the National Institutes of Health. The Government has certain rights in the invention.

BACKGROUND

Tinnitus, the perception of sound that has no external source, is an audiological and neurological condition that impacts an estimated 1 in 7 people. Tinnitus disproportionately impacts those who have served in the armed force, affecting up to two-thirds of the current 1.2 million active duty military service members and over 1.5 million veterans. Tinnitus also increases with age, peaking in people 65 years and older. There is currently no effective "cure" for tinnitus despite the vast amount of research devoted to it. Current treatments are focused on coping strategies, however, while potentially beneficial, this is generally not sufficient for people with moderate to severe tinnitus (at least 20% of people that have tinnitus). For these people, the disorder is severe enough to interfere with daily activities.

Patients with tinnitus exhibit broad changes in brain activity in the auditory system and elsewhere. One of the fundamental characteristics of tinnitus is a dysregulation in the balance of excitatory and inhibitory activity in the central auditory system (CAS). This occurs in response to peripheral deafferentation and can give rise to maladaptive plasticity in the CAS, demonstrated by increased spontaneous neural activity and synchronization despite reduced input from the cochlea. In many cases hyperacusis, the abnormal sensitivity to sound is a comorbid condition commonly found in patients with tinnitus. Hyperacusis is also associated with neural hyperexcitability in the CAS, although in a different pattern than for tinnitus.

There is a need for compounds, compositions, and methods for treating tinnitus. The compounds, compositions, and methods disclosed herein address these and other needs.

SUMMARY

In accordance with the purposes of the disclosed materials and methods, as embodied and broadly described herein, the disclosed subject matter, in one aspect, relates to compositions and methods for treating tinnitus in a subject in need thereof. The methods can include administering a therapeutically effective amount of a compound having a structure represented by Formula I:

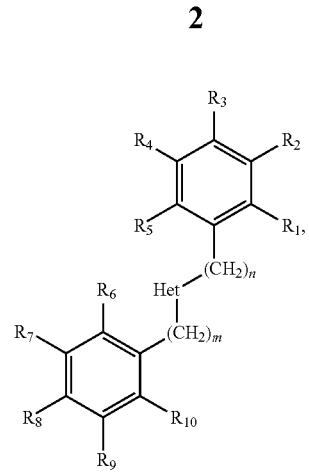

Formula I

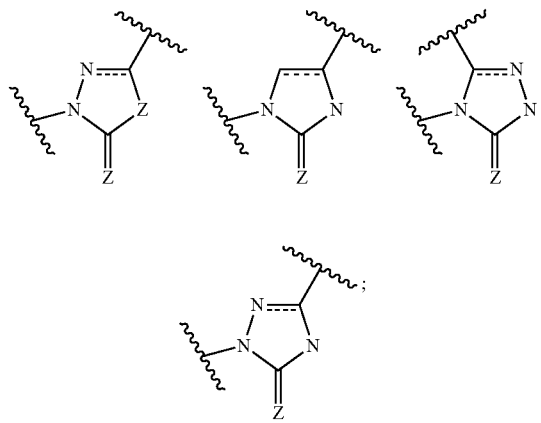

wherein "Het" is a moiety selected from $Z$ is, independently for each occurrence, O, S, or $CH_2$;

$R_1$ is OH or a phosphate containing group;

$R_3$ is hydrogen, halogen, $C_1$-$C_6$ alkyl halide, hydroxyl, $C_1$-$C_6$ hydroxyalkyl, amino, $C_1$-$C_6$ amino alkyl, cyano, or nitro;

$R_4$ is halogen, $C_1$-$C_6$ alkyl halide, hydroxyl, $C_1$-$C_6$ hydroxyalkyl, amino, $C_1$-$C_6$ aminoalkyl, cyano, or nitro;

$R_8$ is hydrogen, halogen, $C_1$-$C_6$ alkyl halide, hydroxyl, $C_1$-$C_6$ hydroxyalkyl, amino, $C_1$-$C_6$ aminoalkyl, cyano, nitro, or a 5-7 membered heterocyclic moiety;

$R_2$, $R_5$, $R_6$, $R_7$, $R_9$, and $R_{10}$ are, independently, hydrogen, halogen, $C_1$-$C_6$ alkyl halide, hydroxyl, $C_1$-$C_6$ hydroxyalkyl, amino, $C_1$-$C_6$ aminoalkyl, $C_1$-$C_6$ alkoxy, cyano, nitro, $C_1$-$C_6$ alkyl, $C_1$-$C_6$ alkenyl, cycloalkyl, cycloalkenyl, heterocycloalkyl, heterocycloalkenyl, aryl, or heteroaryl ring, or two of $R_2$, $R_3$, $R_5$, $R_6$, $R_7$, $R_9$, and $R_{10}$ combine to form a cycloalkenyl, heterocycloalkenyl, aryl, or heteroaryl ring;

n and m each are, independently, 0, 1, or 2; and

---- is a bond that is optionally present, or a nontoxic pharmaceutically acceptable salt or solvate thereof, or a prodrug thereof.

In some embodiments of Formula I, Het is a moiety represented by the structure below

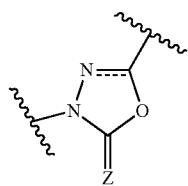

wherein Z is O, S, or CH$_2$. In these embodiments, the compound can be represented by Formula Ia:

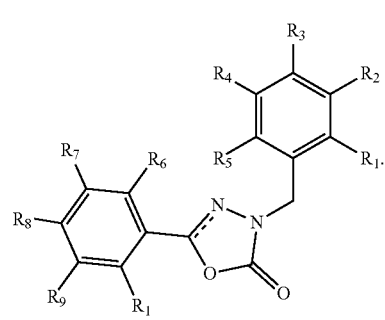

Formula Ia

In some embodiments of Formula I, R$_1$ is OH or a prodrug thereof. In some embodiments of Formula I, the compound is a prodrug represented by Formula Ib:

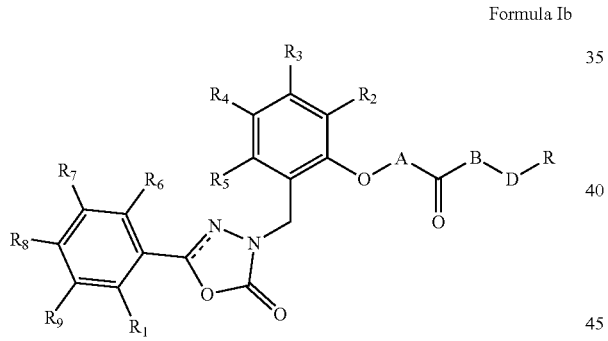

Formula Ib wherein
- A is a direct bond or —CH$_2$O—;
- B is a direct bond or oxygen;
- D is —(CH$_2$)x— or —CH$_2$CHOHCH$_2$—, wherein x is an integer from 1 to 4;
- R is —NR$^a$R$^b$ or —NR$^a$R$^b$R$^c$X in which X is a counter anion; and R$^a$, R$^b$, and R$^c$ each are independently hydrogen or C$_{1-4}$ alkyl;

or a nontoxic pharmaceutically acceptable salt or solvate thereof.

In some embodiments of Formula Ib, both A and B are direct bonds. In other embodiments of Formula Ib, A can be —CH$_2$O—. In other embodiments of Formula Ib, B can be oxygen. In some embodiments of Formula Ib, D can be —(CH$_2$)$_x$—. In other embodiments of Formula Ib, D can be —CH$_2$CHOHCH$_2$—.

The compounds described herein can be represented by a structure below:

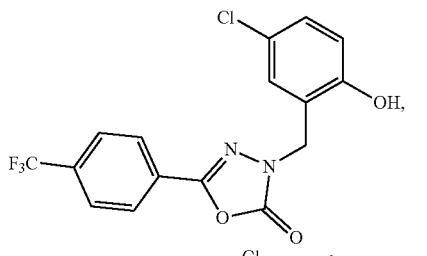

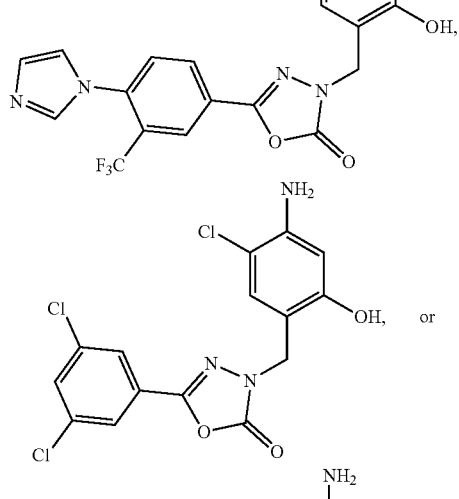

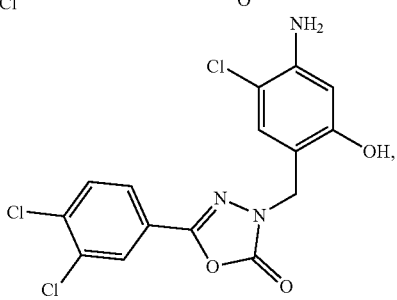

or a nontoxic pharmaceutically acceptable salt or solvate thereof, a derivative thereof, or a prodrug thereof.

The methods disclosed herein can include administration of the compounds to a mammal. The mammal can be a human.

The compound can be administered orally, intravenously, sublingually, ocularly, topically, transdermally, nasally, or intraperitoneally. Preferably, the compound is administered transdermally or orally via a sustained release mechanism.

The method can result in reduction of at least one behavioral correlate of tinnitus, at least one neurophysiological correlate of tinnitus, or a combination thereof. In some examples, the method can result in reduction of hyperactivity in the auditory system.

Pharmaceutical compositions comprising a compound described herein and a pharmaceutically acceptable excipient, wherein the composition provides sustained release of the compound represented by Formula I are also disclosed. In some embodiments, the pharmaceutical composition is in a form for transdermal administration, preferably a transdermal patch. In other embodiments, the pharmaceutical composition is in a form for oral administration, preferably a tablet.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF THE DRAWINGS

FIG. 1A shows startle amplitude plotted as a function of SES intensity. A two-way RM ANOVA indicated a main effect of intensity ($F(1.217, 6.084)=13.34$; $p<0.01$) on startle amplitude. Holm-Sidak post-hoc analysis showed a significant increase in startle amplitude relative to baseline following SS treatment; this was not significantly altered by subsequent BMS-191011 treatment (N=6). FIG. 1B shows a schematic of the GPAIS assay used to probe the presence of tinnitus. When a silent gap is placed prior to the SES, startle amplitude is reduced. Tinnitus reduces the effectiveness of the silent gap in reducing startle amplitude. FIG. 1C shows the percent reduction in startle amplitude by a silent gap, or % Gap PPI, displayed for several carrier frequencies. A two-way RM ANOVA indicated a main effect of treatment for 12-20 kHz carriers ($F(1.239, 6.194)=12.19$; $p<0.05$). % Gap PPI shown for 24 kHz as reference; SS treatment is not expected to induce tinnitus at this frequency. For 12-20 kHz carriers, post-hoc analysis showed a significant decrease in % Gap PPI following SS treatment that was returned to baseline levels by subsequent BMS-191011 treatment (N=6). $*p<0.05$, $**p<0.01$.

FIG. 2A shows the intensity threshold shift for ABRs increased following SS treatment and was not further altered by BMS-191011 treatment. FIG. 2B plots show the quantification of P1 latencies as a function of intensity for 12, 16, 20 and 24 kHz tones. Two-way RM ANOVAs indicated a main effect of treatment for all frequencies (12 kHz: $F(1.629, 17.92)=31.53$; $p<0.0001$; 16 kHz: $F(1.926, 21.19)=40.95$; $p<0.0001$; 20 kHz: $F(1.717, 18.89)=33.40$; $p<0.0001$; 24 kHz: $F(1.663, 16.63)=36.64$; $p<0.0001$, N=8-12). Post-hoc analyses indicated that SS treatment significantly delayed P1 latencies relative to baseline when administered alone or with BMS-191011. In contrast, BMS-191011 treatment minimally altered the effect of SS treatment. FIG. 2C plots show the quantification of P1 amplitudes as a function of intensity for 12, 16, 20 and 24 kHz tones. Two-way RM ANOVAs indicated a main effect of treatment for all frequencies (12 kHz: $F(1.627, 11.46)=15.29$, $p<0.001$; 16 kHz: $F(1.703, 11.92)=46.48$, $p<0.0001$; 20 kHz: $F(1.351, 9.460)=37.97$, $p<0.0001$; 24 kHz: $F(1.181, 8.266)=30.50$, $p<0.001$; N=8-12). Post-hoc analyses indicated that SS treatment significantly reduced P1 amplitudes relative to baseline when administered alone or with BMS-191011. BMS-191011 treatment did not significantly alter the effect of SS treatment. $*p<0.05$, $p<0.01$, $*p<0.001$, $****p<0.0001$.

FIG. 3A shows two-way RM ANOVAs indicated a significant interaction between intensity and treatment for P2 amplitudes in response to 12-20 kHz tones (12 kHz: $F(1.847, 14.16)=5.916$, $p<0.05$; 16 kHz: $F(2.145, 16.45)=14.85$, $p<0.001$; 20 kHz: $F(3.022, 23.17)=9.327$, $p<0.001$). Posthoc analysis indicated that SS treatment increased P2 amplitude at 80 dB relative to baseline when administered alone or with BMS-191011. In contrast, there was a significant reduction in P2 amplitudes for 24 kHz tones in response to treatment ($F(1.158, 11.58)=16.77$; $p<0.01$). FIG. 3B shows for P4 amplitudes, two-way RM ANOVAs indicated a significant interaction between intensity and treatment in response to higher frequencies (20 kHz: $F(3.139, 24.07=3.433$, $p<0.05$; 24 kHz: $F(2.760, 19.32)=3.977$, $p<0.05$). BMS-191011 treatment did not significantly alter the effect of SS treatment on P2 or P4 amplitudes. FIG. 3C show graph of the amplitude of P2 relative to P1 for 60 dB tones show the effect of treatment on gain in the auditory brainstem ($F(1.171, 12.88)=20.80$; $p<0.0001$). Two-way RM ANOVA with post-hoc analysis indicated that SS treatment significantly increased the P2/P1 ratio relative to baseline at all intensities, and that this was unaltered by BMS-191011 treatment. FIG. 3D shows consistent with the P2/P1 ratios, a graph of the amplitude of P4 relative to P1 for 60 dB tones also show an effect of treatment on gain in the auditory brainstem (two-way RM ANOVA; $F(1.1801, 19.81)=16.81$; $p<0.0001$; N=8-12). Post-hoc analyses indicated that SS treatment significantly increased the P4/P1 ratio relative to baseline at all intensities, and that this was unaltered by BMS-191011 treatment. Dotted lines at P2/P1 and P4/P1=1 demarcate equal amplitudes. N=8-12 $*p<0.05$, $p<0.01$, $*p<0.001$.

FIG. 4A shows representative examples of excitatory frequency response areas (eFRAs) before and several hours after topical administration of 10 µM BMS-191011 in a young adult mouse naïve to SS. FIG. 4B shows box plot of the maximal number of spikes per 25 ms stimulus within the receptive field shows a significant decrease in sound-evoked activity after 1-10 (one-way RM ANOVA, $F(1.83, 62.1)=10.63$, $p<0.0001$). Post-hoc analysis (Sidak) comparing each timepoint to baseline show a significant decrease by 1 hour after BMS-191011 administration. FIG. 4C shows box plot of the number of spontaneous spikes per 25 ms shows no significant change after BMS-191011 administration (one-way RM ANOVA, $F(2.72, 106.3)=0.323$).

DETAILED DESCRIPTION

Figure 1A:
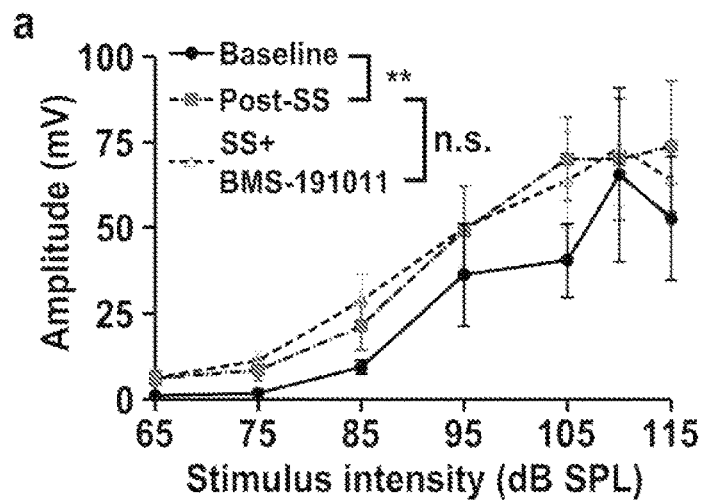
FIGS. 1A-1C show BMS-191011 treatment reduces behavioral manifestations of drug-induced tinnitus.

The compounds, compositions, and methods described herein may be understood more readily by reference to the following detailed description of specific aspects of the disclosed subject matter and the Examples included therein.

Before the present compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, reducing a neurophysiological correlate can include reducing hyperactivity in a subject with tinnitus relative to a standard or a control.

By "treat" or other forms of the word, such as "treated" or "treatment," is meant to administer a composition or to perform a method in order to reduce, inhibit, or eliminate a particular characteristic or event. The term "control" is used synonymously with the term "treat."

The term "therapeutically effective" means the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

Examples of prodrugs that can be used to improve bioavailability include esters, optionally substituted esters, branched esters, optionally substituted branched esters, carbonates, optionally substituted carbonates, carbamates, optionally substituted carbamates, thioesters, optionally substituted thioesters, branched thioesters, optionally substituted branched thioesters, thiocarbonates, optionally substituted thiocarbonates, S-thiocarbonate, optionally substituted S-thiocarbonate, dithiocarbonates, optionally substituted dithiocarbonates, thiocarbamates, optionally substituted thiocarbamates, oxymethoxycarbonyl, optionally substituted oxymethoxycarbonyl, oxymethoxythiocarbonyl, optionally substituted oxymethoxythiocarbonyl, oxymethylcarbonyl, optionally substituted oxymethylcarbonyl, oxymethylthiocarbonyl, optionally substituted oxymethylthiocarbonyl, L-amino acid esters, D-amino acid esters, N-substituted L-amino acid esters, N,N-disubstituted L-amino acid esters, N-substituted D-amino acid esters, N,N-disubstituted D-amino acid esters, sulfenyl, optionally substituted sulfenyl, imidate, optionally substituted imidate, hydrazonate, optionally substituted hydrazonate, oximyl, optionally substituted oximyl, imidinyl, optionally substituted imidinyl, imidyl, optionally substituted imidyl, aminal, optionally substituted aminal, hemiaminal, optionally susbstituted hemiaminal, acetal, optionally substituted acetal, hemiacetal, optionally susbstituted hemiacetal, carbonimidate, optionally substituted carbonimidate, thiocarbonimidate, optionally substituted thiocarbonimidate, carbonimidyl, optionally substituted carbonimidyl, carbamimidate, optionally substituted carbamimidate, carbamimidyl, optionally substituted carbamimidyl, thioacetal, optionally substituted thioacetal, S-acyl-2-thioethyl, optionally substituted S-acyl-2-thioethyl, bis-(acyloxybenzyl)esters, optionally substituted bis-(acyloxybenzyl)esters, (acyloxybenzyl) esters, optionally substituted (acyloxybenzyl)esters, and BAB-esters.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Pharmaceutically acceptable derivative" or "pharmaceutically acceptable salt" refers to a prodrug or salt that is pharmaceutically acceptable and has the desired pharmacological properties. Such derivatives or salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, therapeutic agents, compositions, and methods, examples of which are illustrated in the accompanying Examples.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

As used herein, the term "alkyl" refers to straight-chained, branched, or cyclic, saturated hydrocarbon moieties. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include methyl, ethyl, propyl, isopropyl, 1-methyl-ethyl, butyl, isobutyl, t-butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, 1-ethyl-2-methyl-propyl, pentyl, hexyl, heptyl, octyl, nonyl, decyl, dodecyl, tetradecyl, hexadecyl, eicosyl, tetracosyl, and the like. Alkyl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, and haloalkylaminocarbonyl, provided that the substituents are sterically compatible and the rules of chemical bonding and strain energy are satisfied.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C≡C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C≡C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

As used herein, the term "alkyl halide" or "haloalkyl" refers to straight-chained or branched alkyl groups, wherein these groups the hydrogen atoms may partially or entirely be substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl$C_1$-$C_6$ haloalkylcarbonyl, and haloalkylaminocarbonyl, provided that the substituents are sterically compatible and the rules of chemical bonding and strain energy are satisfied.

As used herein, the term "alkoxy" refers to a group of the formula —O$Z^1$, where $Z^1$ is unsubstituted or substituted alkyl as defined above. In other words, as used herein an "alkoxy" group is an unsubstituted or substituted alkyl group bound through a single, terminal ether linkage. Unless otherwise specified, alkoxy groups wherein $Z^1$ is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-pentoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphtyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, $C_1$-$C_6$ haloalkylcarbonyl, and haloalkylaminocarbonyl, provided that the substituents are sterically compatible and the rules of chemical bonding and strain energy are satisfied.

As used herein, the terms "amine" or "amino" refers to a group of the formula —$NZ^1Z^2$, where $Z^1$ and $Z^2$ can independently be a hydrogen, alkyl, haloalkyl, alkenyl, alkynyl, aryl, heteroaryl, cycloalkyl, cycloalkenyl, heterocycloalkyl, or heterocycloalkenyl group as described above. As used herein, the term "alkylamino" refers to an amino group substituted with one or two unsubstituted or substituted alkyl groups, which may be the same or different. As used herein, the term "haloalkylamino" refers to an alkylamino group wherein the alkyl carbon atoms are partially or entirely substituted with halogen atoms.

As used herein, the term "phosphate-containing" group refers to a salt or ester of an oxygen acid of phosphorus or a phosphorus oxo acid. In its salt form or base form, a phosphate-containing group contains at least one metal ion or an ammonium ion. The phosphate containing group includes partial and complete esters of phosphorus oxo acids. Examples of phosphate-containing groups include a phosphinic acid, phosphonic acid, phosphoric acid, pyrophosphoric phosphinic acid, pyrophosphoric acid groups, partial and complete esters and salts thereof. For example, the phosphate-containing group includes "phosphonyl" which refers to a group of the formula

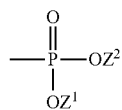

where $Z^1$ and $Z^2$ can independently be a hydrogen, $C_1$-$C_8$ alkyl, $C_1$-$C_8$ haloalkyl, $C_2$-$C_8$ alkenyl, $C_2$-$C_8$ alkynyl, $C_6$-$C_{10}$ aryl, $C_6$-$C_{10}$ heteroaryl, $C_3$-$C_{12}$ cycloalkyl, $C_3$-$C_{12}$ cycloalkenyl, $C_3$-$C_{12}$ heterocycloalkyl, or $C_3$-$C_{12}$ heterocycloalkenyl group as described above. As used herein "alkylphosphonyl" refers to a phosphonyl group substituted with one or two unsubstituted or substituted alkyl groups, which may be the same or different. As used herein, the term "haloalkylphosphonyl" refers to an alkylphosphonyl group wherein the alkyl carbon atoms are partially or entirely substituted with halogen atoms.

As used herein, Me refers to a methyl group; OMe refers to a methoxy group; and i-Pr refers to an isopropyl group.

As used herein, the term "halogen" including derivative terms such as "halo" refers to fluorine, chlorine, bromine and iodine.

The term "hydroxyl" as used herein is represented by the formula —OH.

The term "nitro" as used herein is represented by the formula —$NO_2$.

The term "cyano" as used herein is represented by the formula —CN.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A prodrug refers to a compound that is made more active in vivo. Certain compounds disclosed herein can also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they can be easier to administer than the compound, or parent drug. They can, for instance, be bioavailable by oral administration whereas the parent drug is not. The prodrug can also have improved solubility in pharmaceutical compositions over the parent drug. A wide variety of prodrug derivatives are known in the art, such as those that rely on hydrolytic cleavage or oxidative activation of the prodrug.

Prodrugs of any of the disclosed compounds include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Oligopeptide modifications and biodegradable polymer derivatives (as described, for example, in *Int. J. Pharm.* 115, 61-67, 1995) are within the scope of the present disclosure. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, *Design of Prodrugs*, Elsevier, 1985; and *Bioreversible Carriers in Drug Design*, ed. Edward Roche, American Pharmaceutical Association and Pergamon Press, 1987.

Reference will now be made in detail to specific aspects of the disclosed materials, compounds, compositions, articles, and methods, examples of which are illustrated in the accompanying Examples and Figures.

Compounds and Compositions

Provided herein are compounds, compositions, and methods for treating tinnitus. The compounds disclosed herein are effective opener of the large conductance, calcium-activated $K^+$-channels (BK channel). In some examples, the compounds for treating tinnitus include a 1,3,4-oxadiazol-2(3H)-one structure. For example, the compounds for treating tinnitus can have a structure represented by the general Formula I:

Formula I

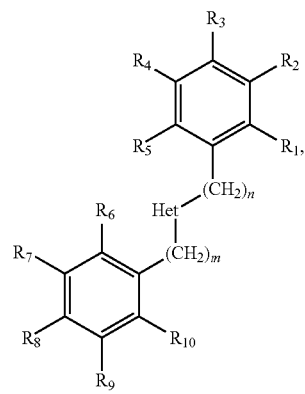

wherein "Het" is a moiety selected from

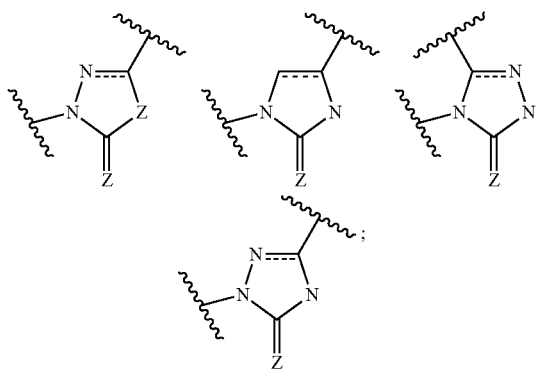

Z is, independently for each occurrence, O, S, or CH$_2$;
R$_1$ is OH or a phosphate containing group;
R$_3$ is hydrogen, halogen, C$_1$-C$_6$ alkyl halide, hydroxyl, C$_1$-C$_6$ hydroxyalkyl, amino, C$_1$-C$_6$ aminoalkyl, cyano, or nitro;
R$_4$ is halogen, C$_1$-C$_6$ alkyl halide, hydroxyl, C$_1$-C$_6$ hydroxyalkyl, amino, C$_1$-C$_6$ aminoalkyl, cyano, or nitro;
R$_8$ is hydrogen, halogen, C$_1$-C$_6$ alkyl halide, hydroxyl, C$_1$-C$_6$ hydroxyalkyl, amino, C$_1$-C$_6$ aminoalkyl, cyano, nitro, or a 5-7 membered heterocyclic moiety;
R$_2$, R$_5$, R$_6$, R$_7$, R$_9$, and R$_{10}$ are, independently, hydrogen, halogen, C$_1$-C$_6$ alkyl halide, hydroxyl, C$_1$-C$_6$ hydroxyalkyl, amino, C$_1$-C$_6$ aminoalkyl, C$_1$-C$_6$ alkoxy, cyano, nitro, C$_1$-C$_6$ alkyl, C$_1$-C$_6$ alkenyl, cycloalkyl, cycloalkenyl, heterocycloalkyl, heterocycloalkenyl, aryl, or heteroaryl ring, or two of R$_2$, R$_3$, R$_5$, R$_6$, R$_7$, R$_9$, and R$_{10}$ combine to form a cycloalkenyl, heterocycloalkenyl, aryl, or heteroaryl ring;
n and m each are, independently, 0, 1, or 2; and
---- is a bond that is optionally present;
a nontoxic pharmaceutically acceptable salt or solvate of Formula I, a derivative thereof, or a prodrug thereof.
In some embodiments of Formula I, the Het moiety can be represented by the structure below

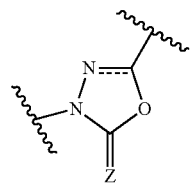

wherein Z is O, S, or CH$_2$. In other examples of Formula I, the Het moiety can be represented by the structure below

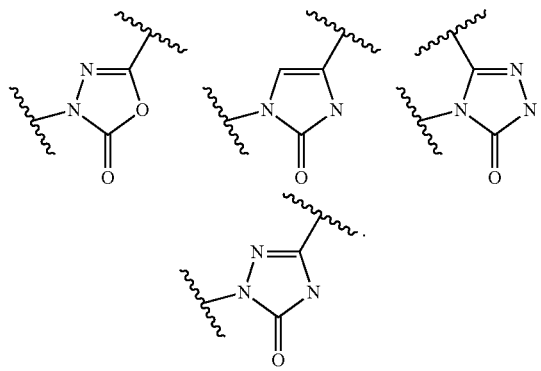

In some embodiments of Formula I, the compound can be represented by Formula Ia:

Formula Ia

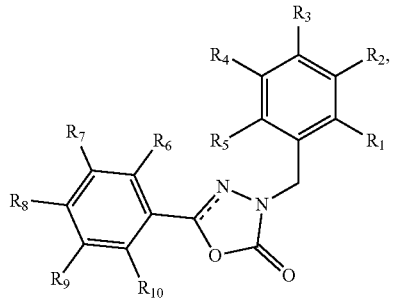

wherein
R$_1$ is OH or a phosphate containing group;
R$_3$ is hydrogen, halogen, C$_1$-C$_6$ alkyl halide, hydroxyl, C$_1$-C$_6$ hydroxyalkyl, amino, C$_1$-C$_6$ aminoalkyl, cyano, or nitro;
R$_4$ is halogen, C$_1$-C$_6$ alkyl halide, hydroxyl, C$_1$-C$_6$ hydroxyalkyl, amino, C$_1$-C$_6$ aminoalkyl, cyano, or nitro;
R$_8$ is hydrogen, halogen, C$_1$-C$_6$ alkyl halide, hydroxyl, C$_1$-C$_6$ hydroxyalkyl, amino, C$_1$-C$_6$ aminoalkyl, cyano, nitro, or a 5-7 membered heterocyclic moiety;
R$_2$, R$_5$, R$_6$, R$_7$, R$_9$, and R$_{10}$ are, independently, hydrogen, halogen, C$_1$-C$_6$ alkyl halide, hydroxyl, C$_1$-C$_6$ hydroxyalkyl, amino, C$_1$-C$_6$ aminoalkyl, C$_1$-C$_6$ alkoxy, cyano, nitro, C$_1$-C$_6$ alkyl, C$_1$-C$_6$ alkenyl, cycloalkyl, cycloalkenyl, heterocycloalkyl, heterocycloalkenyl, aryl, or heteroaryl ring, or two of R$_2$, R$_3$, R$_5$, R$_6$, R$_7$, R$_9$, and R$_{10}$ combine to form a cycloalkenyl, heterocycloalkenyl, aryl, or heteroaryl ring;
n and m each are, independently, 0, 1, or 2; and
---- is a bond that is optionally present;

a nontoxic pharmaceutically acceptable salt or solvate of Formula I, a derivative thereof, or a prodrug thereof.

As described herein, the compounds of Formulas I and Ia can be a prodrug thereof, preferably a water-soluble prodrug thereof. As described herein, the prodrug can be a derivative of the active drug which is converted after administration back to the active drug. More particularly, it can be a derivative of the compounds disclosed herein which may be active drugs and/or which are capable of undergoing hydrolysis (of for example, an ester or methyleneoxy ester moiety) or cleavage so as to release active free drug. The physiologically hydrolyzable groups serve as prodrugs by being hydrolyzed in the body to yield the parent drug per se.

In some embodiments of Formulas I or Ia, $R_1$ can be OH. When $R_1$ is OH, the OH group can be in the form of a salt or a prodrug thereof. In some embodiments of Formulas I, Ia or Ib, $R_1$ can be a phosphate-containing group such as a phosphonyl ester group.

In some embodiments of Formulas I or Ia, the compound can be a prodrug represented by Formula Ib:

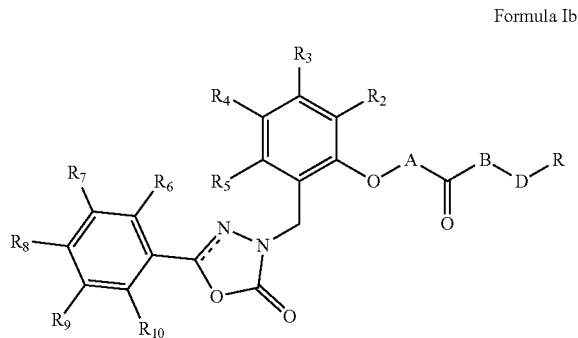

Formula Ib wherein
A is a direct bond or —CH$_2$O—;
B is a direct bond or oxygen;
D is —(CH$_2$)$_x$— or —CH$_2$CHOHCH$_2$—, wherein x is an integer from 1 to 4;
R is hydrogen, —NR$^a$R$^b$ or —NR$^a$R$^b$R$^c$X in which X is a counter anion; and R$^a$, R$^b$, and R$^c$ each are independently hydrogen or C$_{1-4}$ alkyl;
or a nontoxic pharmaceutically acceptable salt or solvate thereof.

In some embodiments of Formula Ib, A can be a direct bond. In some embodiments of Formula Ib, A can be —CH$_2$O—. In some embodiments of Formula Ib, B can be a direct bond. In some embodiments of Formula Ib, B can be oxygen. In some embodiments of Formula Ib, both A and B can be a direct bond. In some embodiments of Formula Ib, D can be —(CH$_2$)$_n$—. In some embodiments of Formula Ib, x is 1, 2, 3, or 4. In some embodiments of Formula Ib, each of R$^a$, R$^b$, and R$^c$ are independently methyl, ethyl, propyl, isopropyl, butyl, isobutyl, or tertbutyl.

In some embodiments of Formulas I, Ia or Ib, $R_3$ can be hydrogen or an amino group. The amino group can be unsubstituted or substituted with a C$_1$-C$_4$ alkyl group. In some examples, $R_3$ is —NH$_2$. In other examples, $R_3$ is hydrogen.

In some embodiments of Formulas I, Ia or Ib, $R_4$ can be a halogen. For example, $R_4$ can be F, Cl, or Br. In some examples, $R_4$ is Cl.

In some embodiments of Formulas I, Ia or Ib, $R_8$ can be selected from hydrogen, halogen, a C$_1$-C$_6$ alkyl halide, or a 5-7 membered heterocyclic moiety. For example, $R_8$ can be selected from a C$_1$-C$_6$ alkyl halide such as a C$_1$-C$_4$ alkyl halide or a C$_1$-C$_2$ alkyl halide. In some examples, $R_8$ can be selected from trifluoromethyl, trifluoroethyl, trifluoropropyl, difluoromethyl, difluoroethyl, difluoropropyl, trichloromethyl, trichloroethyl, trichloropropyl, dichloromethyl, dichloroethyl, or dichloropropyl. In specific examples, $R_8$ can be trifluoromethyl. In other examples, $R_8$ can be a halogen selected from F, Cl, or Br. In specific examples, $R_8$ can be Cl. In further examples, $R_8$ can be a 5-7 membered heterocyclic moiety. For example, $R_8$ can be a 5 membered heterocyclic moiety, such as a diazole moiety (for e.g., pyrazole or imidazole) or a triazole moiety (for e.g., 1,2,3-triazole or 1,2,4-triazole). In even further examples, $R_8$ can be hydrogen.

In some embodiments of Formulas I, Ia or Ib, each of $R_2$, $R_6$ and $R_{10}$, independently, can be selected from hydrogen or a C$_1$-C$_6$ alkyl. For example, each of $R_2$, $R_6$ and $R_{10}$, independently, can be hydrogen, methyl, ethyl, or propyl. In some examples of Formulas I, Ia or Ib, $R_2$, $R_6$ and $R_{10}$ are all hydrogen.

In some embodiments of Formulas I, Ia or Ib, each of $R_2$ can be selected from hydrogen or a C$_1$-C$_6$ alkyl. For example, each of $R_2$ can be hydrogen, methyl, ethyl, or propyl. In some examples of Formulas I, Ia or Ib, each of $R_2$ is hydrogen.

In some embodiments of Formulas I, Ia or Ib, $R_6$ can be selected from hydrogen or a C$_1$-C$_6$ alkyl. For example, $R_6$ can be hydrogen, methyl, ethyl, or propyl. In some examples of Formulas I, Ia or Ib, $R_6$ is hydrogen.

In some embodiments of Formulas I, Ia or Ib, $R_{10}$ can be selected from hydrogen or a C$_1$-C$_6$ alkyl. For example, $R_{10}$ can be hydrogen, methyl, ethyl, or propyl. In some examples of Formulas I, Ia or Ib, $R_{10}$ is hydrogen.

In some embodiments of Formulas I, Ia or Ib, each of $R_7$ and $R_9$, independently, can be selected from hydrogen, a halogen or a C$_1$-C$_6$ alkyl halide. In some examples, $R_7$ can be hydrogen. In other examples, $R_7$ can be a C$_1$-C$_6$ alkyl halide such as a C$_1$-C$_4$ alkyl halide or a C$_1$-C$_2$ alkyl halide. Examples of alkyl halide groups include trifluoromethyl, trifluoroethyl, trifluoropropyl, difluoromethyl, difluoroethyl, difluoropropyl, trichloromethyl, trichloroethyl, trichloropropyl, dichloromethyl, dichloroethyl, or dichloropropyl. In specific examples, $R_7$ can be trifluoromethyl. In further examples, $R_7$ can be a halogen selected from F, Cl, or Br. In specific examples, $R_7$ can be Cl.

In some examples, $R_9$ can be hydrogen. In other examples, $R_9$ can be a C$_1$-C$_6$ alkyl halide such as a C$_1$-C$_4$ alkyl halide or a C$_1$-C$_2$ alkyl halide. In specific examples, $R_9$ can be trifluoromethyl. In further examples, $R_9$ can be a halogen selected from F, Cl, or Br. In specific examples, $R_9$ can be Cl.

In some examples of Formulas I, Ia or Ib, at least one of $R_7$ and $R_9$ is a halogen such as Cl. In other examples of Formulas I, Ia or Ib, both $R_7$ and $R_9$ are halogen. In further examples of Formulas I, Ia or Ib, both $R_7$ and $R_9$ are hydrogen.

In some embodiments of Formulas I, Ia or Ib, n is 1. In some embodiments of Formulas I, Ia or Ib, n is 0. In some embodiments of Formulas I, Ia or Ib, n is 2.

In some embodiments of Formulas I, Ia or Ib, m is 1. In some embodiments of Formulas I, Ia or Ib, m is 0. In some embodiments of Formulas I, Ia or Ib, m is 2.

In some embodiments of Formulas I, Ia or Ib, the compound can be represented by a structure below:

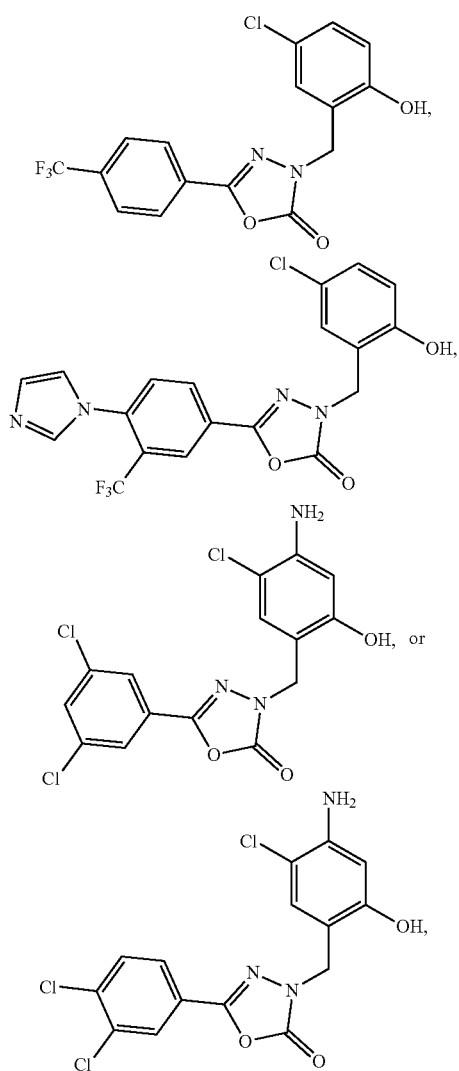

or a nontoxic pharmaceutically acceptable salt or solvate thereof, a derivative thereof, or a prodrug thereof.

Pharmaceutical Compositions

The compounds described herein or pharmaceutically acceptable salt or solvate thereof, a derivative thereof, or a prodrug thereof can be provided in a pharmaceutical composition. In some embodiments, the composition can include a compound of any one of Formulas I, Ia, or Ib.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of a compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

In some embodiments, the pharmaceutical composition can be in a form for transdermal administration. Accordingly, the present disclosure provides a transdermal formulation for treating tinnitus. The transdermal formulation can be configured to provide an extended or sustained release of the active compound. In one aspect, a single dosage of the transdermal formulation can be sufficient to achieve and sustain the active compound blood plasma level of at least 0.5 mg/kg body weight for a duration of at least about 12 hours, or at least about 24 hours, or at least about 2 days. The time frame for achieving the desired blood plasma levels may be the result of such parameters as the type and size of the pharmaceutical formulation, the amount of the compound present in the formulation, and the flux rate achieved by the formulation. Further, the flux rate may be determined in part by the presence of specific types of penetration enhancers. Elements such as patch size, compound content, enhancer amount, and enhancer type may all be coordinated in order to achieve the desired blood plasma levels within a desired amount of time. Other physiological factors, such as variations in individual skin type and permeability may affect the ultimate compound blood plasma level and the time frame in which it is achieved.

Various transdermal formulations can be used for transdermally delivering an active compound disclosed herein. Specific transdermal delivery formulation types include but are not limited to: 1) topical formulations such as ointments, lotions, gels, pastes, mousses, aerosols, and skin creams; 2) transdermal patches such as adhesive matrix patches and liquid reservoir systems; 3) transmucosal tablets such as buccal or sublingual tablets or lozenges; and 4) suppositories. In short, any transdermal administration form is acceptable. In one aspect, the transdermal formulation can be a topical formulation. In some embodiments, the transdermal formulation can be an adhesive matrix patch. In other embodiments, the transdermal formulation can be a liquid reservoir system, or patch.

In addition to the active compound, the transdermal formulation can further include an inert carrier and optionally a permeation enhancer in order to increase the permeability of the active compound into the skin. A wide range of known permeation enhancers are known and include but are not limited to: fatty acids, fatty acid esters, fatty alcohols, fatty acid esters of lactic acid or glycolic acid and their salts, amides, amines, pyrrolidones, glycerol triesters, terpenes, classical surfactants, organic acids, complexing agents, biologics, and mixtures thereof.

Specific examples of acceptable fatty acids include but are not limited to, oleic acid, alkanoic acids, capric acid, hexanoic acid, lactic acid, lauric acid, linoleic acid and mixtures thereof. Specific examples of acceptable fatty acid esters include but are not limited to methyl laurate, glycerol monooleate (GMO), sorbitan nonooleate (SMO), glycerol monolaurate (GML), glycerol monolinoleate (GMLO), isopropyl myristate, isopropyl palmitate, methyl propionate, monoglycerides, propylene glycol monolaurate, sorbitan monolaurate, and mixtures thereof. Specific examples of acceptable fatty alcohols include but are not limited to lauryl alcohol, caprylic alcohol, myristyl alcohol, cetyl alcohol, aliphatic alcohols, linolenyl alcohol, nerolidol, oleyl alcohol, and mixtures thereof. Specific examples of acceptable fatty acid esters of lactic acid or glycolic acid or their salts include but are not limited to lauroyl glycolate, sodium lauryol glycolate, caproyl glycolate, sodium caproyl glycolate, cocyl glycolate, sodium cocyl glycolate, isostearoyl glycolate, tromethamine lauroyl glycolate, lauroyl lactylate, sodium lauroyl lactylate, caproyl lactylate, sodium caproyl lactylate, cocoyl lactylate, sodium cocyl lactylate, isostearoyl lactylate, tromethamine lauryol lactylate, and mixtures thereof.

Specific examples of acceptable amides include but are not limited to lauramide diethanolamide, alkanolamides, ethoxylated alkanolamides, ethylene bisamides, urea, and mixtures thereof. Specific examples of acceptable pyrrolidones include but are not limited to N-methyl-pyrrolidone N-alkyl-pyrrolidones, pyrrolidone carboxylic acids, pyrrolidone carboxylic esters, and mixtures thereof. Specific examples of acceptable classical surfactants include, but are not limited to Brij surfactants, (such as Brij 30, Brij 36T, Brij, 35, Brij 52), Pluronic surfactants, (such as Pluronic F68, and Pluronic L62), Span surfactants, (such as Span 20 and Span 85), Tween surfactants, (Such as Tween 20, Tween 40, and Tween 80), Poloxomer surfactants, Myrj surfactants, bile salts, sodium laurate, sodium lauryl sulfate, and mixtures thereof.

While the transdermal formulation can include a variety of permeation enhancers, no enhancer is necessary in order to achieve the desired blood plasma levels in many instances. Therefore, in one aspect the transdermal formulations can be free of a permeation enhancer, and consist essentially of an amount of the active compound herein sufficient to achieve a desired blood plasma admixed with an inert carrier.

In specific examples, the transdermal delivery formulation may take the form of an occlusive device, such as a transdermal patch, in order to provide an active compound formulation. Such a transdermal patch may either be an adhesive matrix patch, a liquid reservoir system type patch, or a buccal or sublingual tablet. In the case of the adhesive matrix patch, an amount of the active compound sufficient to produce the desired therapeutic blood plasma level is dissolved or suspended in a polymeric phase or carrier. A selected permeation enhancer, or mixture of enhancers may be included in the polymeric phase. The size of an adhesive matrix patch may be adjusted to provide varying dosage amounts, and may vary from about 1 to 200 $cm^2$.

A wide range of adhesives useful in connection with transdermal patches will be known to those skilled in the art of transdermal drug delivery. In one aspect of the invention, acceptable adhesives may include polyacrylate polymers, rubber-based adhesives, and polysiloxanes adhesives. Further details and examples of adhesives which are suitable for use in the present disclosure are set forth in Satas, "The Handbook of Pressure-sensitive Adhesive Technology," $2^{nd}$ ed., pp. 396-456 (1989), which is incorporated herein by reference in its entirety.

Compositions containing an active compound described herein or derivatives thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients. The disclosed compounds can also be incorporated into polymers, examples of which include poly (D-L lactide-co-glycolide) polymer for intracranial tumors; poly[bis(pcarboxyphenoxy) propane:sebacic acid] in a 20:80 molar ratio (as used in GLIADEL); chondroitin; chitin; and chitosan.

In certain embodiments, it is contemplated that the oral compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na-CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release delivery systems. The active compound can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid compound dispersed in a solvent-based polymer solution (suspension method), or by dissolving the compound in a solvent-based polymer solution (dissolution method). One can attach poly (ethylene glycol) to proteins (PEGylation) to increase the in vivo half-life of circulating compound.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

The effective amount of the compounds and compositions or pharmaceutically acceptable salts, derivatives or prodrugs thereof as described herein can be determined by one of ordinary skill in the art and includes exemplary dosage amounts for a mammal of from about 0.5 to about 300 mg/kg of body weight of active compound per day. Alternatively, the dosage amount can be from about 0.5 to about 250 mg/kg of body weight of active compound per day, from about 0.5 to about 200 mg/kg of body weight of active compound per day, from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 0.5 mg/kg of body weight of active compound per day, or about 1 mg/kg of body weight of active compound per day. The expression effective amount, when used to describe an amount of compound in a method, refers to the amount of a compound that achieves the desired pharmacological effect or other effect, for example an amount that results in reduction of a behavioral correlate to tinnitus, an amount that results in reduction of a neurophysiological correlate to tinnitus, or reduction of auditory hyperactivity.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

Kits

Also provided herein are kits for treating tinnitus in a subject. A kit can include any of the compounds or compositions described herein. A kit can further include one or more conventional drug for treating tinnitus. A kit can include a transdermal or oral formulation comprising any one or more of the compounds or compositions described herein. A kit can additionally include directions for use of the kit (e.g., instructions for treating a subject with tinnitus).

Methods of Use

Changes in ion channel function may give rise to and/or mitigate global changes in CAS function by shaping the signaling of individual neurons, each of which interact via local and system-wide ascending and descending circuitry. In particular, the large conductance calcium-activated potassium (BK) channel is expressed throughout the peripheral and central auditory system (CAS) where it shapes the responses of auditory neurons. BK channels are composed of a pore forming α-subunit and an array of auxiliary subunits, with the β1, β4, and γ3 subunits most common in the brain. BK channel activation regulates neurotransmitter release, synaptic integration and action potential firing. In the auditory system, the BK channel is expressed in the cochlea, contributing substantially to the repolarizing current in inner hair cells. In the CAS, the BK channel is expressed in brainstem, modulating signaling in the dorsal cochlear nucleus and at the calyx of Held. Ascending into the inferior colliculus (IC), moderate to high expression of the BK channel α subunit shapes action potential firing and sound-evoked activity. Finally, the auditory cortex (AC) has high expression levels of both BK channel transcripts and protein. BK channels are thus well situated to impact AC function, a region likely necessary for the perception of and negative affective response to tinnitus.

BK channels plays a role in disorders of hyperexcitability, such as temporal lobe epilepsy, tonic-clonic seizures and alcohol withdrawal seizures. Mutations in the BK channel α- and β-subunits are associated with susceptibility to seizures.

Tinnitus is associated with hyperactivity in the CAS. Higher spontaneous activity is apparent as early as the CN and is particularly pronounced in the IC. Changes in the AC are more complex, including elevated spontaneous activity, maladaptive intralaminar activity, and tonotopic remapping.

Provided herein are methods of treating tinnitus in a subject. These methods can include administering an opener of the large conductance, calcium-activated $K^+$-channels (BK channel). In particular, the methods can include administering to a subject an effective amount of one or more of the compounds or compositions described herein, or a pharmaceutically acceptable salt or prodrug thereof. The compounds and compositions described herein or pharmaceutically acceptable salts thereof are useful for treating tinnitus in mammals such as in humans.

As described herein, the compounds and compositions can be adapted for oral, rectal, topical, vaginal, parenteral, intramuscular, intraperitoneal, intraarterial, intrathecal, intrabronchial, subcutaneous, intradermal, intravenous, nasal, buccal or sublingual routes of administration. For oral administration, particular use is made of compressed tablets, pills, tablets, gellules, drops, and capsules. An alternative means of transdermal administration is by use of a skin patch. For example, the active ingredient can be incorporated into a cream consisting of an aqueous emulsion of polyethylene glycols or liquid paraffin. Other forms of administration comprise solutions or emulsions which may be injected intravenously, intraarterially, intrathecally, subcutaneously, intradermally, intraperitoneally or intramuscularly, and which are prepared from sterile or sterilizable solutions. Other forms of administration comprise solutions or emulsions which are in a form suitable for ocular delivery, for example, eye drops, gels, ointments, sprays, creams or specialist ocular delivery devices.

In some examples, the methods disclosed herein can include transdermally administering an amount of an active compound or composition sufficient to treat tinnitus. In other examples, the methods include orally administering an amount of an active compound or composition sufficient to treat tinnitus.

In one aspect, the compounds or compositions administered can be a prodrug of the active compound described herein. A rapid screen to determine the ability of prodrugs to hydrolyze and release the active compound can be conducted as follows. A 1 mg/mL stock solution of the prodrug can be prepared in distilled water or acetonitrile or PEG-400. Plasma from freshly collected rat or human blood can be used in this assay. To 1 mL of plasma at 37° C. can be added 10 µL of stock solution of prodrug and mixed gently. Immediately after the mixing, 100 µL of plasma can then be removed and quenched with 300 µL of acetonitrile (zero time sample). Samples can also be obtained at 30 minutes and quenched immediately. The quenched samples can be centrifuged to obtain a clear supernatant for analysis. The stock solution, T=0 and T=30 samples can be analyzed by a HPLC assay that separates the active compound from the prodrug. Based on the relative peak areas of prodrug and active compound in these samples, different prodrugs can be characterized as fast, moderate and slow release agents.

In further examples, the compounds and compositions disclosed herein can be used in combination with one or more other pharmaceutically active agents. In such cases, the compounds and compositions can be administered consecutively, simultaneously or sequentially with the one or more other pharmaceutically active agents.

The methods described herein can be used to treat drug-induced tinnitus, such as salicylate-induced tinnitus or acoustic trauma-induced tinnitus. In some examples, the methods can cause reduction of at least one behavioral correlate of tinnitus, at least one neurophysiological correlate of tinnitus, or a combination thereof. In specific examples, the methods can cause reduction of hyperactivity in the auditory system in a subject. In some specific examples, the methods can cause reduction of sound-evoked activity in the auditory midbrain. In other specific examples, the methods can cause improvements in gap inhibition. Reduction of at least one behavioral correlate can be determined in a behavioral assay, such as the gap inhibition of the acoustic startle response. Tinnitus would be evident as a loss of gap inhibition, in other words, tinnitus fills in the silent gap resulting in decrease salience and a loss of inhibition or increased startle amplitude. Reduction of at least one neurophysiological correlate can be determined in a neural assay in which a reduction in hyperactivity in spontaneously active neurons would be evident.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Drug Candidates for Treating Tinnitus

Patients with tinnitus exhibit broad changes in brain activity in the auditory system and elsewhere. One of the fundamental characteristics of tinnitus is a dysregulation in the balance of excitatory and inhibitory activity in the central auditory system (CAS). This occurs in response to peripheral deafferentation and can give rise to maladaptive plasticity in the CAS, demonstrated by increased spontaneous neural activity and synchronization despite reduced input from the cochlea. In many cases hyperacusis, the abnormal sensitivity to sound is a comorbid condition commonly found in patients with tinnitus. Hyperacusis is also associated with neural hyperexcitability in the CAS, although in a different pattern than for tinnitus. Because of the dysregulation of neuronal excitability underlying tinnitus and associated disorders, there is a strong interest in targeting ion channels for treatment.

The following methods can be used to induce tinnitus and measure the behavioral manifestations of tinnitus.

Salicylate (SS) model: Known to be an ototoxic drug that induces tinnitus in humans, SS has been used to study transient tinnitus in animal models for over 25 years. SS treatment (250 mg/kg i.p.) dependably produces a percept around 16 kHz in rodents, including in CBA/CaJ mice. This reliable induction of tinnitus in a constrained frequency range provides a high level of reproducibility across animals and experiments. SS can be administrated 2 hours before measuring the behavioral manifestations of tinnitus.

Behavioral assay: The presence of tinnitus may be indicated by a failure to respond to silence embedded in sound stimuli near the tinnitus frequency. A sound pulse-evoked acoustic startle reflex (ASR) is commonly used to determine if an animal can detect silent gaps in narrow-band noise and this method appears to detect tinnitus in humans. Failure of a first sound pulse to suppress a second sound pulse-evoked startle reflex is indicative of tinnitus. This ASR assay has a similar sensitivity for changes in gap detection to a behavioral conditioning paradigm in which animals are trained to response to gaps in noise. Elevations in the ASR amplitude have been linked to the presence of hyperacusis, a disorder often comorbid with tinnitus. Thus, the assay probed possible influences of BK channel function on both tinnitus and hyperacusis.

Methods: SS can be administrated 2 hours before measuring the behavioral manifestations of tinnitus in a mouse model.

The effects of systemic administration of BMS191011, 3-[(5-chloro-2-hydroxyphenyl)methyl]-5-[4-(trifluoromethyl)phenyl]-1,3,4-oxadiazol-2(3H)-one, was then studied in the mouse model. Specifically, BMS191011 was given via i.p. injection (5 mg/kg).

Results: There was a trend for an increase in ASR amplitude after SS treatment, but treatment with BMS191011 did not appear to return this toward baseline. SS-treatment decreased Gap-PPI for stimuli within the tinnitus percept in the 16 kHz region. Administration of BMS191011 returned Gap-PPI to baseline levels, indicating suppression of the tinnitus percept. Thus, the BK channel opener, BMS191011, reduces a behavioral correlate of tinnitus.

BMS191011 also suppressed sound-evoked activity in the IC of control mice. Local administration (topical application over the dura) of BMS191011 shapes sound-evoked activity in the IC of control mice, eventually suppressing activity. A potential mechanism of action then for suppressing tinnitus is reducing hyperactivity in the auditory system.

In summary, systemic treatment (i.p.) with BMS191011 reduced a behavioral indicator of tinnitus.

Example 2: Small Molecule Modulation of the BK Channel Suppresses Drug-Induced Tinnitus Abstract: Tinnitus is the phantom perception of sound that has no external source. A neurological signature of tinnitus is a dysregulation in the balance between excitatory and inhibitory activity in the central auditory system (CAS), leading to neuronal hyperexcitability. This characteristic hyperexcitability guides an interest in regulating neuronal excitability via potassium channels, like the large conductance, calcium-activated potassium (BK) channel, to reduce tinnitus. To test whether BK channel openers are able to suppress drug-induced tinnitus, the 1,3,4 oxadiazole BMS-191011 was given to young adult CBA mice that had been administered 250 mg/kg sodium salicylate (SS) to induce tinnitus. Systemic treatment with BMS-191011 reduced behavioral manifestations of SS-induced tinnitus, probed via the gap-in-noise startle response method. BMS-191011 treatment suppressed sound-evoked activity in the auditory midbrain, suggesting that the reduction in tinnitus arose predominantly from BMS-191011 action in higher auditory structures. Together, this example support the utility of BK channel openers in reducing central auditory processing changes that promote the formation of the tinnitus percept.

Introduction: Evidence from animal models and humans suggests that tinnitus arises after peripheral injury leads to a focal loss of cochlear output. Loss of cochlear output is commonly caused by noise exposure, aging, or ototoxic drugs. Administration of the ototoxic drug, sodium salicylate, reliably induces reversable peripheral hearing loss and tinnitus in both humans and animal models. Multiple modes of action support salicylate-induced changes in central auditory system (CAS) function. Direct peripheral effects lead to reduced cochlear output and abnormal NMDA receptor activation, increasing cochlear thresholds. These peripheral effects support tinnitus. A direct central effect also enhances sound-evoked hyperactivity in the CAS. This latter action is linked to hyperacusis, an intolerance to loud sounds that is highly comorbid with tinnitus. While the entirety of salicylate effects is unlikely to be shared across all tinnitus etiologies, it provides a highly uniform model for studying the modulation of tinnitus, increased central gain, and hyperactivity in the CAS.

Following a loss of cochlear output, enhanced neural activation in the CAS is linked to the formation of a tinnitus percept, and hyperacusis, across modes of induction. As neuronal hyperexcitability in the CAS is a fundamental characteristic of tinnitus, there is a general interest in regulating neuronal excitability via potassium channels to reduce tinnitus and hyperacusis. The large conductance, calcium-activated potassium (BK) channel has been a target of interest for other brain disorders of neuronal excitability like temporal lobe epilepsy, tonic-clonic seizures and alcohol withdrawal seizures. BK channels are composed of a pore forming α-subunit and an array of auxiliary subunits, with the β1, β4, and γ3 subunits most common in brain. The BK channel regulates neurotransmitter release, synaptic integration and action potential firing in the nervous system. Expression of the channel throughout the peripheral and central auditory system is well situated to impact the tinnitus percept, as BK channel activity can regulate input into, and local activity within, the AC where sound perception arises.

This example employed a unique BK channel opener, the 1,3,4 oxadiazole, BMS-191011. Originally developed for treating stroke, BMS-191011 has high brain-availability, and higher affinity and specificity for the BK channel than Maxipost. The current example showed that systemic treatment with BMS-191011 reduced behavioral manifestation of salicylate-induced tinnitus in young adult CBA mice. Neurophysiological assessment showed that BMS-191011 treatment did not influence SS-induced changes in auditory brainstem responses (ABRs). But, BMS-191011 did suppress sound-evoked activity in the auditory midbrain and SS. Thus, these findings indicate that positive modulation of BK channel function reduces a drug-induced tinnitus percept. Further, the results provide first insights into how BK channel modulation may be influencing tinnitus—such as by reducing neural activity in rostral auditory brain regions. Overall, this example shows that BK channel openers are suitable for counteracting/reversing central auditory processing changes underlying the tinnitus percept.

Results: Behavioral sensorimotor gating assays were utilized to probe central auditory processing changes before and after SS administration in young adult CBA/CaJ mice. Modification of the acoustic startle reflex (ASR), elicited by wideband noise stimuli, provided a functional readout of changes in sensorimotor gating. First, startle amplitude was measured in response to multiple intensities of an acoustic startle elicitor. SS administration increased the intensity-response function relative to baseline (FIG. 1a). To test whether the systemic administration of the BK channel opener, BMS-191011, suppressed the SS-induced increase in startle amplitudes, BMS-191011 was administered after SS, 1 hour before behavioral testing. BMS-191011 treatment did not reverse the effects of SS administration on the startle amplitude intensity-response function (FIG. 1a). BMS-191011 treatment also did not alter startle amplitudes when administered alone. Thus, BMS-191011 does not alter baseline sensorimotor gating, nor SS-augmented sensorimotor responses suggesting enhanced acoustic sensitivity. This latter indication of hyperactivity in central auditory processing is consistent with the presence of hyperacusis following SS administration.

Figure 1B:
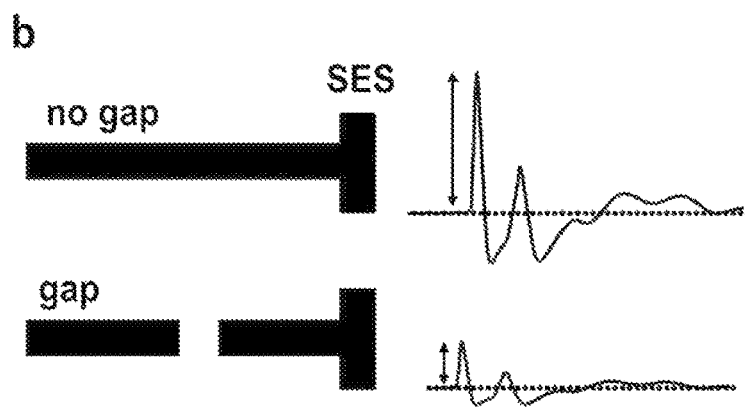
Figure 1C:
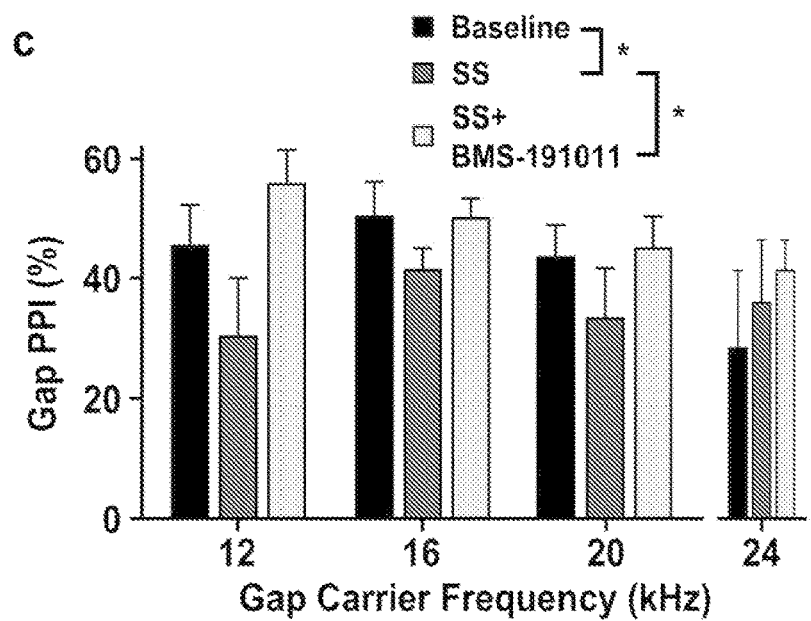

Next, modification of ASRs by acoustic pre-pulse stimuli probed the presence of tinnitus following SS administration. When an audible stimulus occurs shortly (e.g., 100 ms) before the startle elicitor, the ASR is inhibited, and this is referred to as pre-pulse inhibition. In the GPIAS paradigm (FIG. 1b), a silent gap in noise inhibits the startle response relative to a no-gap condition (Gap-PPI). The degree to which the ASR amplitude is reduced is directly related to the salience of the gap pre-pulse. Failure of this silent gap to suppress a subsequently elicited startle reflex, indicated by a reduction in Gap-PPI, is thus indicative of a tinnitus percept near the pre-pulse frequency. SS administration reduced Gap-PPI relative to baseline when the silent gap was placed in a 12-20 kHz carrier (FIG. 1c). Thus, SS administration induced tinnitus percepts in the 12-20 kHz range, roughly centered around 16 kHz. In contrast, SS administration did not influence Gap-PPI for a 24 kHz carrier, outside of the expected frequency range of the tinnitus percept. Administration of BMS-191011 returned SS-suppressed Gap-PPIs to baseline levels for 12-20 kHz carriers. There was no effect on Gap-PPI for a 24 kHz carrier. Although BMS-191011 treatment reversed SS-induced changes in Gap-PPI functions, these functions were not significantly altered from baseline when BMS-191011 treatment was administered alone. Together, these findings indicate that BMS-191011 treatment reduces behavioral manifestation of SS-induced tinnitus.

Figures 2A, 2B, 2C:
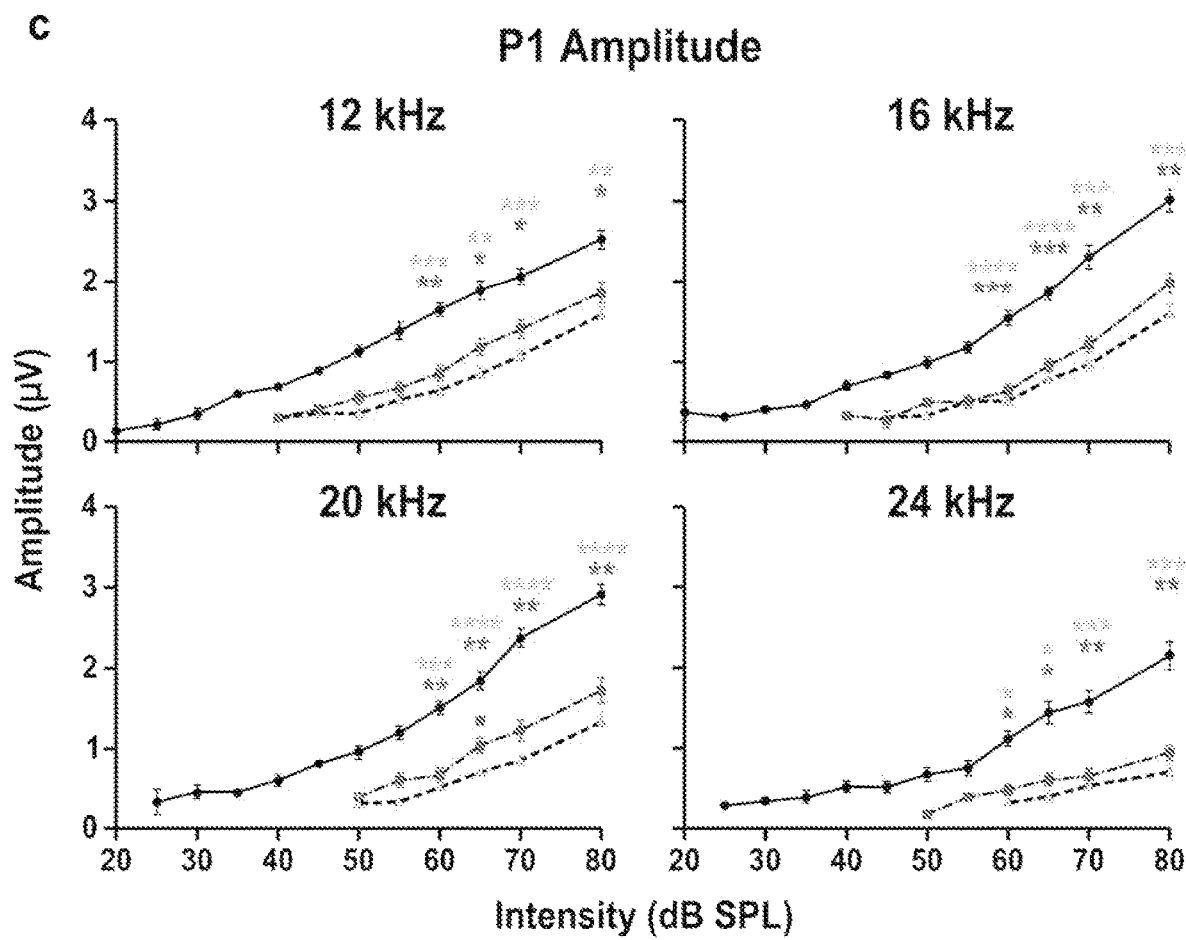
FIGS. 2A-2C show BMS-190111 treatment does not enhance SS-suppressed AN output.

SS-induced tinnitus is associated with reduced auditory nerve (AN) output combined with hyperactivity starting in the cochlear nucleus (CN) and continuing into ascending CAS structures. A set of neurophysiological assays began to probe which of these tinnitus-related activity changes are substantially reversed by BMS-191011 treatment. First, ABRs were recorded before and after SS administration to observe tinnitus-related changes in cochlear and brainstem auditory processing. SS administration produced a broad-spectrum reduction in AN output (Chen, 1995), indicated by increased ABR thresholds, by ~20 dB, across the frequency spectrum (FIG. 2a). Reduced AN output following SS administration was further indicated by longer P1 latencies, particularly at lower intensities, and reduced P1 amplitudes relative to baseline (FIG. 2b-d). When BMS-191011 was administered after SS, 1 hour before ABR recordings, BMS-191011 treatment did not significantly alter SS-induced changes in ABR threshold changes, shifts in P1 latencies or decreased P1 amplitudes (FIG. 2b-d). Thus, BMS-191011 treatment did not significantly impact the SS-induced decrease in AN output.

Figures 3A, 3B, 3C, 3D:
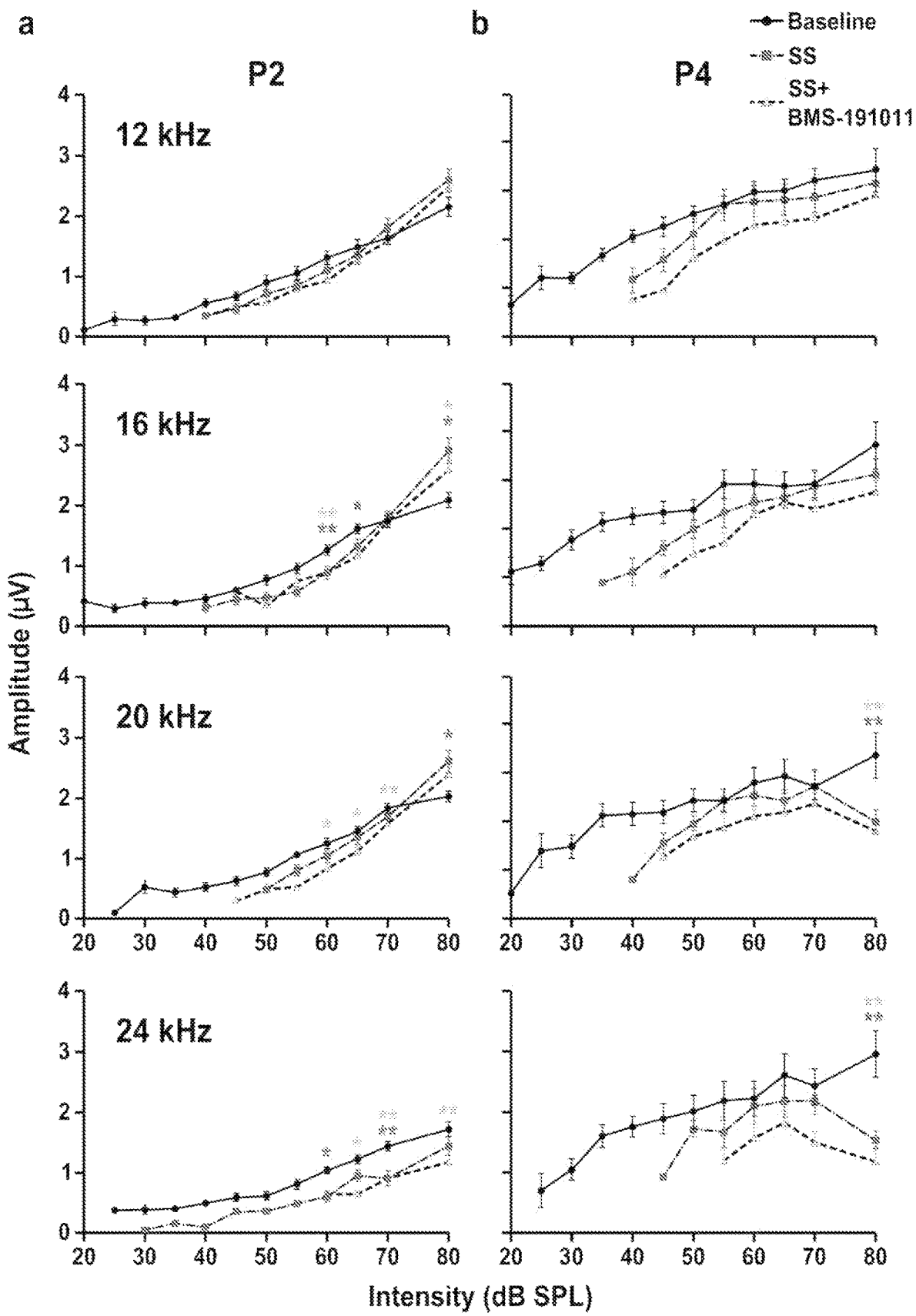
FIGS. 3A-3D show BMS-191011 treatment does not suppress the increased gain in early auditory structures caused by SS treatment. Plots show the quantification of P2 (FIG. 3A) and P4 (FIG. 3B) amplitudes as a function of intensity.

Despite reduced AN activity, tinnitus is associated with amplified sound-evoked activity near the tinnitus percept in caudal auditory structures for both humans and SS-treated mice. To measure activity in the brainstem through lemniscal pathways, ABR P2 and P4 amplitudes were measured before and after SS administration. P2 either increased or stayed the same following SS administration for frequencies near the expected tinnitus range (12-20 kHz) when delivered at higher intensities (60-80 dB SPL), despite a reduction in AN output for these same stimuli (FIG. 3a vs. FIG. 2c). As a result, the ratios of P2 to P1 amplitudes were substantially increased by SS for 12-20 kHz stimuli (FIG. 3c). Ascending in the auditory pathway, the effects of SS on gain were more subtle. P4 amplitudes only remained constant following SS administration for 12-16 kHz stimuli (FIG. 3b), though the P4/P1 amplitude ratios still increased for 12-20 kHz stimuli (FIG. 3d). Subsequent treatment with BMS-191011, after SS administration, did not substantively alter the SS-induced enhancement of P2 or P2/P1 amplitudes (FIG. 3a,c), nor similar indications of increased gain in the P4 measures (FIG. 3b,d). Together these findings suggest that BMS-191011 treatment does not counteract the enhanced neural activity induced by SS administration in the brainstem through lemniscal auditory regions. As such, BMS-191011 treatment likely counteracts auditory processing changes that support the tinnitus percept in rostral CAS regions.

Figure 4A:
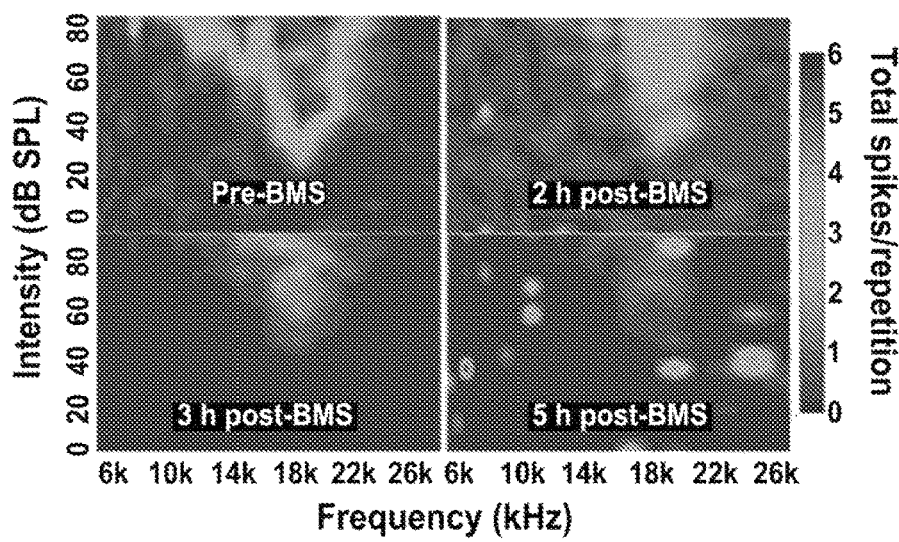
FIGS. 4A-4C show topical administration of BMS-191011 suppresses neural activity in the auditory midbrain.
Figure 4B:
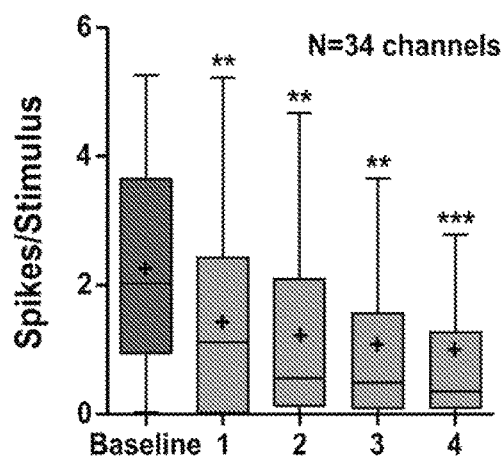
Figure 4C:
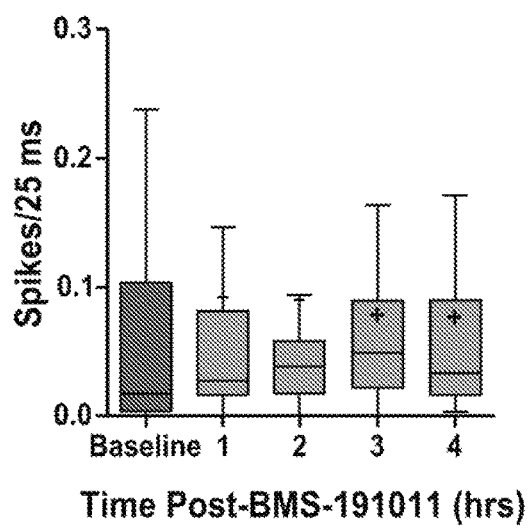

Hyperexcitability is particularly pronounced in the auditory midbrain following tinnitus induction. To test whether BMS-191011 treatment may suppress tinnitus via influences on auditory midbrain function, multi-channel neurophysiological recordings were made in the IC of awake CBA/CaJ mice. First, recordings were made in adult animals that were not administered SS. Multi-unit excitatory frequency-response areas (eFRA) before and after topical administration of BMS-191011 (1 μL of a 1-10 μM solution) at the dura showed a reduction in sound-evoked activity (FIG. 4a). To quantify this change, the maximum number of spikes evoked by a tone stimulus was calculated before and after treatment. The suppression of sound-evoked activity was significant by 1 hour after treatment, and maintained a ~50% reduction from hours 2-4. In contrast, spontaneous activity remained unchanged.

Overall, these data indicate that BMS-191011 treatment counteracts behavioral manifestation of SS-induced tinnitus, returning Gap-PPIs for 12-20 kHz pre-pulse stimuli to baseline values. While changes in peripheral and brainstem auditory processing also support the presence of tinnitus centering around 16 kHz, BMS-191011 treatment did not alter ABR markers of tinnitus following SS administration. Instead, BMS-191011 may counteract more rostral tinnitus-associated changes in auditory processing. Local administration of BMS-191011 suppressed sound-driven activity in the midbrain, which typically expresses particularly pronounced hyperexcitability following SS administration.

Discussion: The example reported herein explored the effects of systemic administration of the BK channel opener, BMS-191011, on behavioral and neurophysiological biomarkers of tinnitus. SS treatment uniformly generates CAS hyperexcitability and dependably produces a narrowband tinnitus percept in rodents. This reliable induction of tinnitus in a constrained frequency range provides a high level of reproducibility across animals and experiments. A sensorimotor gating behavioral read-out of central auditory function showed that SS treatment induced a narrow-band tinnitus percept, roughly centered around 16 kHz, which was reduced by treatment with BMS-191011. Interestingly, BMS-191011 did not influence the behavioral manifestation of a form of salicylate-induced hyperactivity more indicative of hyperacusis than tinnitus. Further neurophysiological assessment showed that BMS-191011 treatment did not substantially influence sound-evoked activity in caudal auditory regions, even though ABR markers of tinnitus-related activity were evident. Instead, influence of BMS-191011 treatment on SS-induced tinnitus likely arose through action in auditory structures rostral to the leminiscal pathways.

3-Fluorooxindoles, initially developed by Bristol-Myers Squibb as BK channel openers, were found to be a potent KCNQ channel modulators. The current findings show that an oxadiazolone-class BK channel opener with higher BK channel affinity and specificity than the 3-fluorooxindoles also reduced behavioral manifestations of SS-induced tinnitus in rodents. BMS-191011 is well-tolerated in animals without signs of negative cardiac effects, such as change in heart rate or blood pressure. Structure-activity relationship studies have explored analogs with the goal of improving solubility while maintaining high brain availability and specific BK channel activity. Improved aqueous solubility, facilitating oral availability, has been achieved by generating cleavable prodrugs that convert to the active compound. Thus, one may be expected to find new drug candidates in this class that, like other drugs and drug candidates with BK channel activity in the therapeutic dose range, will pass safety assessments in clinical trials.

BK channels are well situated in the auditory system to impact the tinnitus percept as the expression patterns allow regulation of input into and local activity within the AC, where sound perception arises. In the cochlea, the BK channel contributes to the repolarizing current in hair cells. In the CAS, the BK channel is expressed in brainstem, modulating signaling in the dorsal cochlear nucleus and at the calyx of Held. The IC has moderate to high BK channel expression where it shapes action potential firing and sound-evoked activity. Finally, the AC has high expression levels of both BK channel transcripts and protein. However, despite this potential for a broad impact on auditory signal processing, this example suggests that BK channel openers may modulate tinnitus-related activity in a more focused manner. Tinnitus is associated with reduced AN output, combined with increased gain and neural activity starting in the CN, and particularly pronounced in the auditory midbrain. Changes in the auditory cortex (AC) are more complex, including elevated activity, maladaptive intralaminar activity, and tonotopic remapping. The BK channel provides a repolarizing force, and in some circuits, positive modulation of BK channel function counteracts hyperexcitability in the brain. In this example, BMS-191011 treatment did not influence reduced AN output and increased gain in caudal CAS structures associated with SS-induced tinnitus. This is consistent with previous finding that BK channel modulation did not strongly influence driven activity in the periphery and brainstem, at least for static signals. Instead, suppression of neural activity in the midbrain and cortex by BK channel openers may support the reversal of salicylate/tinnitus-related CAS activity. Here it was found that BMS-191011 suppresses sound-evoked activity in the auditory midbrain, consistent with a similar effect by Maxipost. Additionally, it has been shown that BK channel activation reduces tinnitus-like hyperactivity in an in vitro neuronal network derived from mouse auditory cortex. Thus, the reduction in sound-driven activity in the auditory midbrain, along with sound processing changes in other rostral regions by BMS-191011 support the normalization of CAS processing following tinnitus induction by SS. and other modes of induction.

Overall, this example supports new drug candidates that target the BK channel for treating tinnitus. Now there is strong support for the ability of BK channel openers to counteract biomarker(s) of tinnitus following salicylate administration. To further test the translation potential more broadly for tinnitus, it will be important to employ acoustic trauma models. The etiology is mixed for patients with tinnitus, but noise exposure is the most common underlying contributing factor. Nonetheless, these findings are consistent with counteracting CAS hyperexcitability, generally considered a thing by BK channels. Additionally, our neurophysiological assessment indicates that this reduction in SS-induced tinnitus arose predominantly from BMS-191011 action in higher auditory structures, providing a first insight into the mechanism through which BK channel openers may counteract tinnitus generally.

Methods

Animals. CBA/CaJ mice bred in house were housed 3-4 per cage with litter-mates in Sealsafe Plus GM500 cages (36.9×15.6×13.2 cm) connected to a Aero70 Techniplast Smart Flow system (West Chester, PA). The animal housing cages were maintained at 24±1° C. with a relative humidity range of 65±3%, and a 12 hr light cycle (on at 0700 hr). Tap water and mouse chow were available ad libitum. All procedures were performed between 0800 and 1600 hours, and were approved by the Institutional Animal Care and Use Committee at the University of South Florida.

General Procedure. Mice underwent sequential assessment of the effect of treatment (baseline; sodium salicylate; sodium salicylate with BMS-191011). Baseline measures were acquired before sodium salicylate (SS) administration so that mice served as their own controls. Tinnitus was induced transiently by intraperitoneal (i.p.) injection of 250 mg/kg SS (concentration: 25 mg/mL 0.9% saline). SS induces tinnitus in humans, and SS-treated animals share markers of tinnitus with humans. Behavioral or neurophysiological manifestations of tinnitus were assessed 2 hours following SS injection, and were completed within 3.5 hours. Jastreboff et al. reported that after an i.p. injection of SS in rats, the maximum levels in blood serum occurred 1.5 hours later, while the maximum levels in the perilymph and spinal fluid reached maximum levels within 2-4 hours. However, behavioral manifestations of tinnitus are observed up to 48 hours following administration (cite). BMS-191011 (Sigma Aldrich) was administered i.p. (0.5 mg/kg) or topically (1 µL of 1-10 µM) at the dura over the auditory midbrain.

Behavioral Assays. Behavioral assessment were performed as described previously (Longenecker and Galazyuk, 2011; Lowe and Walton, 2015), and as briefly outlined below. The animals were acclimated to the testing room by placing the home cage in the testing room 30 min prior to testing. The acoustic startle response (ASR), a transient motor response to a startle eliciting stimulus (SES), was converted to voltage by placing mice on a custom-built platform connected to piezoelectric transducers located inside a sound attenuated chamber. SESs were 20-ms Gaussian broadband noise bursts (1-ms rise/fall time), filtered at 500 Hz-40 kHz. To measure threshold and amplitude of the ASR, the intensity of the SES was varied between 55-115 dB SPL. Ten trials were run for each stimulus in order to acquire the startle input-output function.

Modification of the ASR by stimuli placed before the SES is typically observed as a reduction in startle amplitude or pre-pulse inhibition (Hoffman and Ison, 1980; Ison and Hoffman, 1983). To probe the tinnitus percept (Longenecker and Galazyuk, 2012; Turner, 2007), Turner and colleagues used a relatively long silent gap imbedded in an ongoing narrow band noise (NBN) placed before the SES; various center frequencies of the NBN were used. The paradigm as a whole is referred to as the gap pre-pulse inhibition of the acoustic startle (GPIAS). The silent gap is demonstrably perceived; but, if the tinnitus pitch is in the region of the pitch of the ongoing NBN, the animal will presumably be impaired at detecting the gap (Turner, et al 2007). The presence of tinnitus is then indicated by a reduction in pre-pulse inhibition to the gap stimulus, or Gap-PPI, when the gap carrier pitch is near the tinnitus frequency (Turner, 2007). To perform the GPIAS assay, in this study the SES (presented at 100 dB SPL) was preceded by a 150-ms, 70-dB narrow band noise (⅓ octave) centered at 6, 12, 16, 20, or 24 kHz. During gap trials, a 50-ms silent gap was inserted 100 ms before the SES. Ten trials of each stimulus were presented to obtain the Gap PPI function. Mice that demonstrated decreased Gap-PPI to any frequency carrier for in the GPAIS paradigm were considered tinnitus positive, and advanced to the treatment phases of the experiment.

ABR Assays. To obtain an electrophysiological measure of auditory evoked activity in the auditory nerve and brainstem, ABR assays were performed as described previously (Longenecker and Galazyuk, 2011; Lowe and Walton, 2015), and as briefly outlined below. Animals were anesthetized with i.p. administration of ketamine (120 mg/kg) and xylazine (10 mg/kg). Respiration was monitored during testing and used to guide administration of supplemental anesthesia. Body temperature was kept constant at 37° C. using a feedback-controlled heating pad (Physitemp TCAT2-LV Controller, Clifton, NJ).

ABRs were recorded using BioSig software in a soundproof booth lined with echo-attenuating acoustic foam. ABRs were evoked by 256 tone burst stimuli. Tone bursts were 3 msec in duration (1-ms rise/fall time, alternating polarity) presented at 6, 12, 16, 20, 24, and 36 kHz at a rate of 29 per second, attenuated in 5 dB steps from 80 dB SPL to 15 dB below threshold or 5 dB SPL, whichever was lower. Threshold was determined by visual inspection as the lowest intensity level which produced a defined peak in two replicates. Peaks 1-5 (P1-5) were detected and measured in the ABR waveforms using custom designed MATLAB software.

IC neurophysiological recordings. Surgery and extracellular recordings were collected and analyzed by a method identical to a procedure used in a previous study. The right IC was located stereotaxically and exposed via a small (<1.0 mm) craniotomy. Prior to recording, chlorprothixene (Taractin®, 5-12 µl/g i.m.) was administered to prevent involuntary movement via inhibition of parasympathetic nerve impulses. The animal was then secured in a custom stereotaxic frame (Newport-Klinger) in a heated (34° C.) chamber lined with sound-absorbing foam (Sonex®). Multi-unit extracellular activity was recorded using vertically oriented single shank silicon acute penetrating 16-channel electrodes with an impedance ranging from 1.2 to 2.1 MΩ (Type-A, 3 mm×100 μm; NeuroNexus Technologies). Excitatory frequency response areas (eFRAs) from all active channels were acquired simultaneously using 2 to 64 kHz, 25 ms (5 ms rise/fall) tone burst stimuli presented at 0 to 80 dB SPL in 5 dB steps. A total of 2125 frequency and intensity combinations were presented pseudo-randomly five times each at a rate of 10/s. The change in the driven response due to treatment was assessed via maximum number of spikes per stimulus within the boundary of each eFRA.

Statistics. Data are presented as mean±SEM or as box plots denoting mean, median, and distribution range of the data. Statistical analysis was performed in GraphPad (GraphPad Software, La Jolla, CA). Mixed model ANOVA and Holm-Sidak post-hoc analysis evaluated the effects of treatment. Alpha was set at 0.05 for all statistical tests.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A method of treating tinnitus in a subject in need thereof, the method comprising administering a therapeutically effective amount of a compound having a structure represented by Formula I:

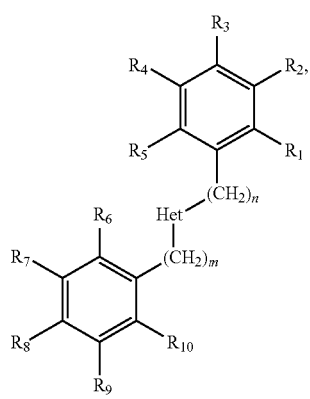

Formula I wherein "Het" is a moiety selected from

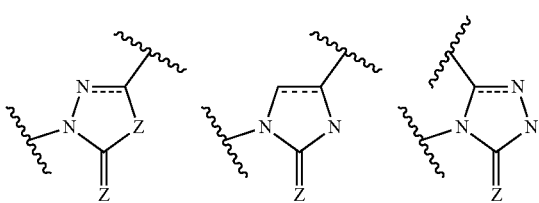

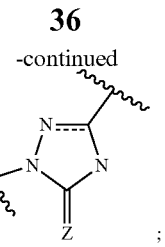

$Z$ is, independently for each occurrence, O, S, or $CH_2$;

$R_1$ is OH or a phosphate containing group;

$R_3$ is hydrogen, halogen, $C_1$-$C_6$ alkyl halide, hydroxyl, $C_1$-$C_6$ hydroxyalkyl, amino, $C_1$-$C_6$ aminoalkyl, cyano, or nitro;

$R_4$ is halogen, $C_1$-$C_6$ alkyl halide, hydroxyl, $C_1$-$C_6$ hydroxyalkyl, amino, $C_1$-$C_6$ aminoalkyl, cyano, or nitro;

$R_8$ is hydrogen, halogen, $C_1$-$C_6$ alkyl halide, hydroxyl, $C_1$-$C_6$ hydroxyalkyl, amino, $C_1$-$C_6$ aminoalkyl, cyano, nitro, or a 5-7 membered heterocyclic moiety;

$R_2$, $R_5$, $R_6$, $R_7$, $R_9$, and $R_{10}$ are, independently, hydrogen, halogen, $C_1$-$C_6$ alkyl halide, hydroxyl, $C_1$-$C_6$ hydroxyalkyl, amino, $C_1$-$C_6$ aminoalkyl, $C_1$-$C_6$ alkoxy, cyano, nitro, $C_1$-$C_6$ alkyl, $C_1$-$C_6$ alkenyl, cycloalkyl, cycloalkenyl, heterocycloalkyl, heterocycloalkenyl, aryl, or heteroaryl ring, or two of $R_2$, $R_3$, $R_5$, $R_6$, $R_7$, $R_9$, and $R_{10}$ combine to form a cycloalkenyl, heterocycloalkenyl, aryl, or heteroaryl ring;

n and m each are, independently, 0, 1, or 2; and

---- is a bond that is optionally present, or a nontoxic pharmaceutically acceptable salt or solvate thereof, or a prodrug thereof.

2. The method of claim 1, wherein Het is a moiety represented by the structure below

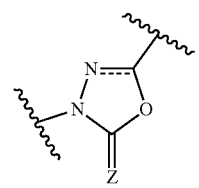

wherein Z is O, S, or $CH_2$.

3. The method of claim 1, wherein the compound is represented by Formula Ia:

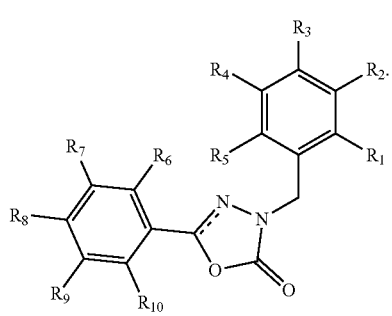

Formula Ia

4. The method of claim 1, wherein $R_1$ is OH or a prodrug thereof.

5. The method of claim 1, wherein the compound is a prodrug represented by Formula Ib:

Formula Ib wherein
- A is a direct bond or —CH$_2$O—;
- B is a direct bond or oxygen;
- D is —(CH$_2$)x— or —CH$_2$CHOHCH$_2$—, wherein x is an integer from 1 to 4;
- R is —NR$^a$R$^b$ or —NR$^a$R$^b$R$^c$X in which X is a counter anion; and R$^a$, R$^b$, and R$^c$ each are independently hydrogen or C$_{1-4}$ alkyl;

or a nontoxic pharmaceutically acceptable salt or solvate thereof.

6. The method of claim 1, wherein R$_3$ is selected from hydrogen or amino.

7. The method of claim 1, wherein R$_4$ is a halogen.

8. The method of claim 1, wherein R$_8$ is selected from hydrogen, halogen, a C$_1$-C$_6$ alkyl halide, or a 5-7 membered heterocyclic moiety.

9. The method of claim 1, wherein the compound is represented by a structure below:

or a nontoxic pharmaceutically acceptable salt or solvate thereof, or a prodrug thereof.

10. The method of claim 1, wherein the compound is administered transdermally.

11. The method of claim 1, wherein the method treats drug-induced tinnitus or acoustic trauma-induced tinnitus.

12. The method of claim 1, wherein each of R$_2$, R$_5$, R$_6$, and R$_{10}$ is independently selected from hydrogen or C$_1$-C$_6$ alkyl.

13. The method of claim 1, wherein R$_7$ and R$_9$ are independently selected from hydrogen, a halogen or a C$_1$-C$_6$ alkyl halide.

* * * * *